(12) United States Patent
Ylitalo et al.

(10) Patent No.: US 9,247,736 B2
(45) Date of Patent: Feb. 2, 2016

(54) ANTIMICROBIAL ADHESIVE FILMS (75) Inventors: Caroline M. Ylitalo, Stillwater, MN (US); Mahfuza B. Ali, Mendota Heights, MN (US); Christopher B. Walker, Jr., Saint Paul, MN (US); Gerald R. A. Hofmann, Oakdale, MN (US); Matthew T. Scholz, Woodbury, MN (US); Alphonsus V. Pocius, Maplewood, MN (US); Linda K. M. Olson, Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1030 days.

(21) Appl. No.: 12/094,758

(22) PCT Filed: Dec. 14, 2006

(86) PCT No.: PCT/US2006/047780
§ 371 (c)(1),
(2), (4) Date: May 22, 2008

(87) PCT Pub. No.: WO2007/070650
PCT Pub. Date: Jun. 21, 2007

(65) Prior Publication Data
US 2009/0130157 A1 May 21, 2009

Related U.S. Application Data (60) Provisional application No. 60/743,036, filed on Dec. 14, 2005.

(51) Int. Cl.
| | |
|---|---|
| A01N 25/34 | (2006.01) |
| A01N 33/12 | (2006.01) |
| B32B 27/18 | (2006.01) |
| C08J 5/18 | (2006.01) |
| B32B 7/06 | (2006.01) |
| B32B 7/12 | (2006.01) |
| B32B 27/08 | (2006.01) |
| B32B 27/30 | (2006.01) |
| B32B 27/32 | (2006.01) |
| B32B 27/36 | (2006.01) |
| C09J 133/14 | (2006.01) |
| A01N 59/16 | (2006.01) |
| C08F 220/34 | (2006.01) |

(52) U.S. Cl.
CPC .............. *A01N 25/34* (2013.01); *A01N 59/16* (2013.01); *B32B 7/06* (2013.01); *B32B 7/12* (2013.01); *B32B 27/08* (2013.01); *B32B 27/18* (2013.01); *B32B 27/308* (2013.01); *B32B 27/32* (2013.01); *B32B 27/36* (2013.01); *C08J 5/18* (2013.01); *C09J 133/14* (2013.01); *B32B 2264/10* (2013.01); *B32B 2264/105* (2013.01); *B32B 2307/412* (2013.01); *B32B 2307/7145* (2013.01); *B32B 2307/75* (2013.01); *B32B 2405/00* (2013.01); *B32B 2479/00* (2013.01); *C08F 220/34* (2013.01); *C08J 2357/00* (2013.01)

(58) Field of Classification Search
None
See application file for complete search history.

(56) References Cited

U.S. PATENT DOCUMENTS

| | | |
|---|---|---|
| 2,449,274 A | 9/1948 | Broll |
| 2,502,881 A | 4/1950 | Parker |
| 2,537,124 A | 1/1951 | Earle et al. |
| 3,832,459 A | 8/1974 | Berkeley |
| 3,926,830 A | 12/1975 | Horiguchi et al. |
| 4,070,194 A | 1/1978 | Arakawa |
| 4,070,510 A | 1/1978 | Kahn |
| 4,071,645 A | 1/1978 | Kahn |
| 4,231,370 A | 11/1980 | Mroz et al. |
| 4,308,625 A | 1/1982 | Kitko |
| 4,353,866 A | 10/1982 | Wong |
| 4,384,869 A | 5/1983 | Wong |
| 4,420,412 A | 12/1983 | Wong |
| 4,441,928 A | 4/1984 | Iijima |
| 4,499,001 A | 2/1985 | Eoga |
| 4,502,605 A | 3/1985 | Wloszczyna |
| 4,578,357 A | 3/1986 | Melpolder |
| 4,584,192 A | 4/1986 | Dell et al. |
| 4,699,885 A | 10/1987 | Melpolder et al. |

(Continued)

FOREIGN PATENT DOCUMENTS

| | | |
|---|---|---|
| AU | 4904672 | 5/1974 |
| DE | 2004019687 | 4/2005 |
| EP | 0 075 934 | 4/1986 |
| EP | 0 549 145 | 6/1993 |
| EP | 0 488 980 | 7/2001 |

(Continued)

OTHER PUBLICATIONS

Decker, C. The Use of UV Irradiation in Polymerization. Polymer International 1998, 45, 133-141.*

(Continued)

*Primary Examiner* — Susan Tran
*Assistant Examiner* — Jessica Worsham
(74) *Attorney, Agent, or Firm* — Nicole J. Einerson (57) ABSTRACT

A multi-layer film for reducing microbial contamination on a surface. The multi-layer film can include a core layer having a first surface and a second surface opposite the first surface, an adhesive layer disposed adjacent the first surface of the core layer, and an antimicrobial layer disposed adjacent the second surface. The antimicrobial layer can include a cross-linked matrix and an antimicrobial agent dispersed within the cross-linked matrix, where the cross-linked matrix is derived from a polymerizable precursor comprising a material selected from the group consisting of a polymerizable monomer, a polymerizable polymer having a molecular weight of about 1,000 or less, and combinations thereof.

29 Claims, 1 Drawing Sheet

(56) References Cited

U.S. PATENT DOCUMENTS

| | | | |
|---|---|---|---|
| 4,717,671 A | 1/1988 | Melpolder | |
| 4,783,340 A | 11/1988 | McDonell et al. | |
| 4,793,988 A | 12/1988 | Casey et al. | |
| 4,954,544 A | 9/1990 | Chandaria | |
| 4,965,063 A | 10/1990 | Casey et al. | |
| 5,057,303 A | 10/1991 | Casey | |
| 5,064,635 A | 11/1991 | Casey | |
| 5,110,492 A | 5/1992 | Casey | |
| 5,125,956 A | 6/1992 | Korte et al. | |
| 5,154,917 A | 10/1992 | Ibrahim et al. | |
| 5,174,995 A | 12/1992 | Davis | |
| 5,196,243 A | 3/1993 | Kawashima | |
| 5,223,245 A | 6/1993 | Ibrahim et al. | |
| 5,234,974 A | 8/1993 | Calhoun et al. | |
| 5,288,486 A | 2/1994 | White | |
| 5,357,989 A | 10/1994 | Gathani | |
| 5,408,022 A * | 4/1995 | Imazato et al. | 526/259 |
| 5,409,977 A | 4/1995 | Sitaramiah et al. | |
| 5,413,789 A * | 5/1995 | Hagiwara et al. | 424/409 |
| 5,418,013 A | 5/1995 | Detrick et al. | |
| 5,420,197 A | 5/1995 | Lorenz et al. | |
| 5,421,898 A | 6/1995 | Cavanagh | |
| 5,454,886 A | 10/1995 | Burrell et al. | |
| 5,460,647 A | 10/1995 | Snedeker et al. | |
| 5,460,802 A | 10/1995 | Asami et al. | |
| 5,460,833 A | 10/1995 | Andrews et al. | |
| 5,464,470 A | 11/1995 | Brachman et al. | |
| 5,470,585 A | 11/1995 | Gilchrist | |
| 5,476,913 A | 12/1995 | Kourai | |
| 5,478,382 A | 12/1995 | Miller et al. | |
| 5,482,654 A | 1/1996 | Luttrell et al. | |
| 5,489,331 A | 2/1996 | Miller et al. | |
| 5,492,558 A | 2/1996 | Miller et al. | |
| 5,494,987 A * | 2/1996 | Imazato et al. | 526/263 |
| 5,532,029 A | 7/1996 | Fuerst et al. | |
| 5,532,290 A | 7/1996 | Newington et al. | |
| 5,547,662 A | 8/1996 | Khan et al. | |
| 5,548,010 A | 8/1996 | Franer | |
| 5,567,420 A | 10/1996 | McEleney et al. | |
| 5,567,753 A | 10/1996 | Shuman et al. | |
| 5,569,461 A | 10/1996 | Andrews | |
| 5,585,407 A | 12/1996 | Patel et al. | |
| 5,586,643 A | 12/1996 | Zabron et al. | |
| 5,612,324 A | 3/1997 | Guang Lin et al. | |
| 5,667,303 A | 9/1997 | Arens et al. | |
| 5,680,962 A | 10/1997 | McEleney et al. | |
| 5,681,575 A | 10/1997 | Burrell et al. | |
| 5,695,857 A | 12/1997 | Burrell et al. | |
| 5,710,141 A | 1/1998 | Lin et al. | |
| 5,746,814 A | 5/1998 | Malhotra et al. | |
| 5,747,011 A | 5/1998 | Ross et al. | |
| 5,753,062 A | 5/1998 | Jansz et al. | |
| 5,753,210 A | 5/1998 | McEleney et al. | |
| 5,753,251 A | 5/1998 | Burrell et al. | |
| 5,766,615 A | 6/1998 | Narayanan | |
| 5,770,255 A | 6/1998 | Burrell et al. | |
| 5,817,325 A | 10/1998 | Sawan et al. | |
| 5,837,275 A | 11/1998 | Burrell et al. | |
| 5,849,311 A | 12/1998 | Sawan et al. | |
| 5,929,160 A | 7/1999 | Krepski et al. | |
| 5,958,383 A | 9/1999 | McEleney et al. | |
| 5,958,440 A | 9/1999 | Burrell et al. | |
| 5,985,308 A | 11/1999 | Burrell et al. | |
| 5,998,431 A | 12/1999 | Tseng et al. | |
| 6,007,797 A | 12/1999 | Bell et al. | |
| 6,017,553 A | 1/2000 | Burrell et al. | |
| 6,024,976 A | 2/2000 | Miranda et al. | |
| 6,080,490 A | 6/2000 | Burrell et al. | |
| 6,086,858 A | 7/2000 | McEleney et al. | |
| 6,102,205 A | 8/2000 | Greff et al. | |
| 6,126,931 A | 10/2000 | Sawan et al. | |
| 6,146,618 A | 11/2000 | Bell et al. | |
| 6,146,651 A | 11/2000 | Kritzler | |
| 6,146,654 A | 11/2000 | Kubo | |
| 6,150,004 A | 11/2000 | Oikawa et al. | |
| 6,162,533 A | 12/2000 | Onozawa | |
| 6,170,564 B1 | 1/2001 | Steele | |
| 6,197,814 B1 | 3/2001 | Arata | |
| 6,238,686 B1 | 5/2001 | Burrell et al. | |
| 6,239,048 B1 | 5/2001 | Wilson et al. | |
| 6,261,541 B1 | 7/2001 | Karpov et al. | |
| 6,264,936 B1 | 7/2001 | Sawan et al. | |
| 6,267,590 B1 | 7/2001 | Barry et al. | |
| 6,267,976 B1 | 7/2001 | Barnhart et al. | |
| 6,290,936 B1 | 9/2001 | Ross et al. | |
| 6,296,863 B1 | 10/2001 | Trogolo et al. | |
| 6,299,799 B1 | 10/2001 | Craig | |
| 6,306,419 B1 | 10/2001 | Vachon et al. | |
| 6,306,810 B1 | 10/2001 | Cheung et al. | |
| 6,333,093 B1 | 12/2001 | Burrell et al. | |
| 6,340,663 B1 | 1/2002 | Deleo et al. | |
| 6,342,212 B1 | 1/2002 | Schuette et al. | |
| 6,365,130 B1 | 4/2002 | Barry et al. | |
| 6,391,226 B1 | 5/2002 | Chauvette et al. | |
| 6,454,813 B1 | 9/2002 | Chan | |
| 6,462,127 B1 | 10/2002 | Ingrisch et al. | |
| 6,467,897 B1 | 10/2002 | Wu et al. | |
| 6,482,423 B1 | 11/2002 | Beerse et al. | |
| 6,504,583 B2 | 1/2003 | Li et al. | |
| 6,544,621 B1 | 4/2003 | Schuette et al. | |
| 6,554,156 B1 | 4/2003 | Chong | |
| 6,582,715 B1 | 6/2003 | Barry et al. | |
| 6,583,176 B2 | 6/2003 | Arata | |
| 6,584,668 B2 | 7/2003 | Green et al. | |
| 6,613,728 B1 | 9/2003 | Sirianni et al. | |
| 6,641,829 B1 | 11/2003 | Green et al. | |
| 6,653,522 B1 | 11/2003 | Blumenthal et al. | |
| 6,667,082 B2 | 12/2003 | Bamore et al. | |
| 6,673,761 B2 | 1/2004 | Mitra et al. | |
| 6,677,287 B1 | 1/2004 | Willman et al. | |
| 6,726,584 B2 | 4/2004 | Iggulden | |
| 6,730,294 B1 | 5/2004 | Kritzler | |
| 6,730,654 B2 | 5/2004 | Godfroid et al. | |
| 6,733,766 B2 | 5/2004 | Gott et al. | |
| 6,741,523 B1 | 5/2004 | Bommarito et al. | |
| 6,772,708 B2 | 8/2004 | Klofta et al. | |
| 6,802,891 B2 | 10/2004 | Kritzler | |
| 6,814,816 B2 | 11/2004 | Achar et al. | |
| 6,838,078 B2 | 1/2005 | Wang et al. | |
| 6,841,527 B2 | 1/2005 | Mitra et al. | |
| 6,884,741 B2 | 4/2005 | Batdorf | |
| 6,894,095 B2 | 5/2005 | Russo et al. | |
| 6,905,711 B1 | 6/2005 | Tullo et al. | |
| 6,911,243 B2 | 6/2005 | Sher et al. | |
| 6,916,480 B2 | 7/2005 | Anderson et al. | |
| 6,926,745 B2 | 8/2005 | Scheuing et al. | |
| 6,951,834 B2 | 10/2005 | Mitra et al. | |
| 7,049,367 B2 | 5/2006 | Mazanek et al. | |
| 7,053,029 B2 | 5/2006 | MacDonald et al. | |
| 7,323,163 B2 | 1/2008 | Wang | |
| 7,459,167 B1 | 12/2008 | Sengupta | |
| 2002/0142036 A1 * | 10/2002 | Rupprecht et al. | 424/484 |
| 2003/0118733 A1 | 6/2003 | Jackson et al. | |
| 2003/0147960 A1 | 8/2003 | Lin et al. | |
| 2003/0157147 A1 | 8/2003 | Hoge et al. | |
| 2003/0175438 A1 | 9/2003 | Reeve | |
| 2003/0191036 A1 | 10/2003 | MacDonald et al. | |
| 2004/0043686 A1 | 3/2004 | Batdorf | |
| 2004/0044299 A1 | 3/2004 | Utsugi | |
| 2004/0137815 A1 | 7/2004 | Ellis et al. | |
| 2004/0180093 A1 * | 9/2004 | Burton et al. | 424/489 |
| 2004/0234561 A1 | 11/2004 | Ansmann | |
| 2005/0000642 A1 | 1/2005 | Everaerts et al. | |
| 2005/0003163 A1 * | 1/2005 | Krishnan | 428/190 |
| 2005/0025668 A1 | 2/2005 | Katsigras et al. | |
| 2005/0047961 A1 | 3/2005 | Bains et al. | |
| 2005/0048856 A1 | 3/2005 | Hauser | |
| 2005/0065048 A1 | 3/2005 | MacDonald et al. | |
| 2005/0080158 A1 | 4/2005 | Ong et al. | |
| 2005/0089539 A1 | 4/2005 | Scholz et al. | |
| 2005/0095266 A1 | 5/2005 | Perichaud et al. | |
| 2005/0101511 A1 | 5/2005 | Zocchi | |
| 2005/0129742 A1 | 6/2005 | Bringley et al. | |
| 2005/0129766 A1 | 6/2005 | Bringley et al. | |

(56) References Cited

U.S. PATENT DOCUMENTS

| | | | |
|---|---|---|---|
| 2005/0129929 A1 | 6/2005 | Patton et al. | |
| 2005/0129937 A1 | 6/2005 | Patton et al. | |
| 2005/0137540 A1 | 6/2005 | Villanueva et al. | |
| 2005/0191326 A1 | 9/2005 | Melker | |
| 2005/0202066 A1* | 9/2005 | Arata | 424/443 |
| 2005/0227893 A1 | 10/2005 | Johnson et al. | |
| 2005/0233930 A1 | 10/2005 | Cheung | |
| 2005/0249791 A1 | 11/2005 | Hobbs | |
| 2005/0255016 A1 | 11/2005 | Svendsen et al. | |
| 2005/0272335 A1 | 12/2005 | Johnson et al. | |
| 2006/0008912 A1 | 1/2006 | Simon et al. | |
| 2006/0030512 A1 | 2/2006 | Hart | |
| 2006/0040835 A1 | 2/2006 | Newkirk et al. | |
| 2006/0127425 A1 | 6/2006 | Walls et al. | |
| 2006/0134163 A1* | 6/2006 | Bagwell et al. | 424/422 |
| 2006/0293205 A1 | 12/2006 | Chung | |
| 2007/0048356 A1 | 3/2007 | Schorr | |
| 2007/0275101 A1 | 11/2007 | Lu et al. | |
| 2008/0026026 A1 | 1/2008 | Lu et al. | |
| 2008/0075951 A1 | 3/2008 | Qiu | |
| 2008/0095965 A1 | 4/2008 | Paiva et al. | |

FOREIGN PATENT DOCUMENTS

| | | |
|---|---|---|
| EP | 0 875 146 | 7/2002 |
| EP | 1 400 574 | 3/2004 |
| EP | 1 443 099 | 8/2004 |
| EP | 1 457 529 | 9/2004 |
| FR | 2043995 | 5/1969 |
| GB | 1073462 | 11/1967 |
| GB | 1553132 | 9/1979 |
| GB | 2 372 939 | 9/2002 |
| JP | 60-170674 | 4/1985 |
| JP | 05-058825 | 3/1993 |
| JP | 93049712 | 7/1993 |
| JP | 09-316369 | 12/1997 |
| JP | 10-204776 | 8/1998 |
| JP | 11-034240 | 2/1999 |
| JP | 11-269448 | 10/1999 |
| JP | 2001-019730 | 1/2001 |
| JP | 2002-241418 | 8/2002 |
| JP | 2002-327005 | 11/2002 |
| JP | 2003-55108 | 2/2003 |
| JP | 2004-143374 | 5/2004 |
| JP | 2004-269836 | 9/2004 |
| JP | 2005-319240 | 11/2005 |
| JP | 2006-111815 | 4/2006 |
| JP | 2006-299214 | 11/2006 |
| WO | WO 84/01102 | 3/1984 |
| WO | WO 86/05391 | 9/1986 |
| WO | WO 00/61107 | 10/2000 |
| WO | WO 00/71183 | 11/2000 |
| WO | WO 01/43549 | 6/2001 |
| WO | WO 01/46900 | 6/2001 |
| WO | WO 01/80920 | 11/2001 |
| WO | WO 02/50241 | 6/2002 |
| WO | WO 02/092336 | 11/2002 |
| WO | WO 03/018732 | 3/2003 |
| WO | WO 03/054045 | 7/2003 |
| WO | WO 2004/100664 | 11/2004 |
| WO | WO 2004/103071 | 12/2004 |
| WO | WO 2005/061022 | 7/2005 |
| WO | WO 2005/107455 | 11/2005 |
| WO | WO 2007/058880 | 5/2007 |
| WO | WO 2007/070649 | 6/2007 |
| WO | WO 2007/070650 | 6/2007 |
| WO | WO 2007/100653 | 9/2007 |
| WO | WO 2008/157323 | 12/2008 |

OTHER PUBLICATIONS http://www.merriam-webster.com/dictionary/matrix Feb. 23, 2011.*
http://www.britannica.com/EBchecked/topic/369081/materials-science/32304/Thermoplastics Feb. 14, 2011.*
*The Wiley Encyclopedia of Packaging Technology*, pp. 400-406 (John Wiley & Sons, 1986).
Richards, E.G., *An Introduction to Physical Properties of Large Molecules in Solution*, IUPAB Biophysics Series, Cambridge University Press, Cambridge, (1980), 6 pages.
Barton, A.F.M., *Handbook of Solubility and Other Cohesion Parameters*, 2nd Ed. CRC Press, Boca Raton, FL, (1991), 6 pages.
*Polymer Handbook*, 3rd Ed., J. Brandrup & E.H. Immergut, Eds. John Wiley, NY pp. 519-557 (1989).
Barton, A.F.M., *Handbook of Polymer-Liquid Interaction Parameters and Solubility Parameters*, CRC Press, Boca Raton, FL, (1990), 5 pages.
ASTM E2180-01; Standard Test Method for Determining the Activity of Incorporated Antimicrobial Agent(s) in Polymeric or Hydrophobic Materials, 2004, 3 pages.

* cited by examiner

ANTIMICROBIAL ADHESIVE FILMS

CROSS-REFERENCE TO RELATED APPLICATIONS

Priority is claimed to U.S. Provisional Patent Application No. 60/743,036, filed Dec. 14, 2005, the disclosure of which is incorporated herein by reference in its entirety.

FIELD OF THE INVENTION

The present invention relates to antimicrobial films. In particular, the present invention relates to antimicrobial adhesive films for use on surfaces to reduce the risk of contamination by undesired microorganisms.

BACKGROUND

Contamination by microorganisms can have dramatic impact on-human life and health. During everyday routines, people continuously come into contact with a variety of surfaces that are contaminated with one or more types of microorganisms, some of which may be pathogens. Such surfaces may include countertops, tables, and food preparation surfaces in restaurants, splash guards and conveyor belts in food processing plants, public facilities, display applications, and a variety of surfaces in healthcare settings. Contamination with pathogenic microorganisms in such locations may result in the spread of disease and infections to people, which correspondingly endangers human lives and increases health care costs.

To counter the spread of undesired microorganisms, contaminated surfaces are typically cleaned and sanitized. While this provides an immediate reduction in concentration of microorganisms on given surfaces, the surfaces must be repeatedly cleaned and sanitized on a frequent basis to continue to prevent contamination by microorganisms. Accordingly, there is a need for a durable means for reducing microbial contamination that is easy to use and is effective at reducing microbial contamination over extended periods of time.

BRIEF SUMMARY OF THE INVENTION

The present invention relates to a multi-layer film for reducing contamination on a surface, by microorganisms, and a method of making the multi-layer film. The multi-layer film can include a core layer having a first surface and a second surface opposite the first surface, an adhesive layer disposed adjacent the first surface of the core layer, and an antimicrobial layer disposed adjacent the second surface. The antimicrobial layer can include a cross-linked polymeric matrix and an antimicrobial agent dispersed within the cross-linked matrix, where the cross-linked matrix can be derived from a polymerizable precursor comprising a material selected from the group consisting of polymerizable monomer, polymerizable polymer having a molecular weight of about 1,000 or less, and combinations thereof.

Figure 1:
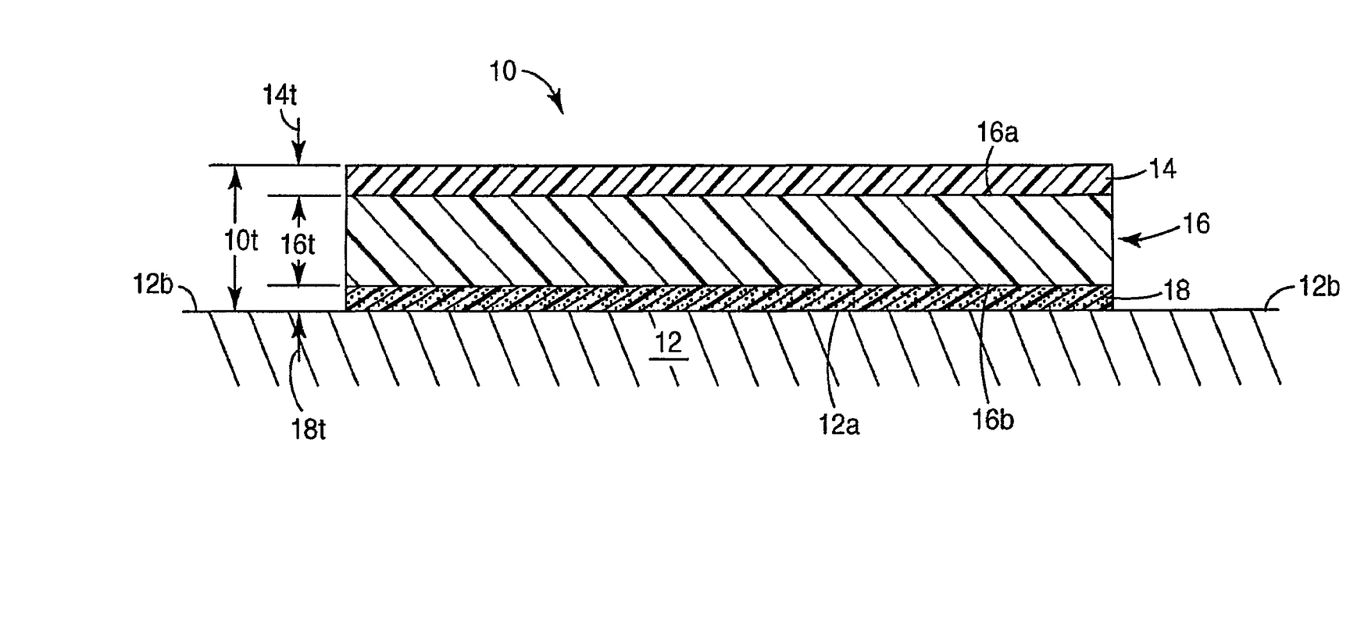
FIG. 1 is a side sectional view of a multi-layer film of the present invention.

While the above-identified FIG. 1 sets forth one embodiment of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. FIG. 1 may not be drawn to scale.

DETAILED DESCRIPTION

FIG. 1 is a side sectional view of multi-layer film 10 of the present invention adhered to surface 12. Multi-layer film 10 is an antimicrobial adhesive film that includes antimicrobial hardcoat layer 14, core layer 16, and adhesive layer 18. As shown, core layer 16 includes top surface 16a and bottom surface 16b, where antimicrobial hardcoat layer 14 is disposed adjacent top surface 16a and adhesive layer 18 is disposed adjacent bottom surface 16b. Directional terms such as "top" and "bottom" are used for ease of discussion, and are not intended to be limiting.

Surface 12 may be any surface that may incur contamination by microorganisms, such as table and counter tops, food preparation surfaces, surfaces found in publicly used locations and facilities (e.g., public telephones, public transportation, and public lavatory facilities), touch-screen displays, door handles, light switches, and surfaces found in healthcare settings (e.g., bed rails and side tables). While surface 12 is shown as a flat, planar surface, multi-layer film 10 may also be coated on/applied to curved and irregular shaped surfaces. As used herein and in the appended claims, the term "microorganism," "microbe," or a derivative thereof, is used to refer to any microscopic organism, including without limitation, one or more of bacteria, viruses, algae, fungi and protozoa. In some cases, the microorganisms of particular interest are those that are pathogenic, and the term "pathogen" is used herein to refer to any pathogenic microorganism.

Surface 12 includes segments 12a and 12b, where segment 12a is the portion of surface 12 that is disposed below multi-layer film 10, and segments 12b are exposed portions of surface 12. Segment 12a is any portion of surface 12 that is at risk of contamination by microorganisms. In some embodiments, segment 12a extends across an entire area of a given surface 12 (e.g., touch-screen displays). In such embodiments, multi-layer film 10 can extend across the entire area of surface 12 to reduce microbial contamination of any portion of surface 12.

Multi-layer film 10 may be adhered to segment 12a of surface 12 to reduce microbial contamination on segment 12a of surface 12 for extended periods of time (e.g., days, weeks, or months, rather than hours). In use, adhesive layer 18 of multi-layer film 10 is laminated on surface 12 such that antimicrobial hardcoat layer 14 faces away from surface 12. Prior to adhering multi-layer film 10, surface 12 may be cleaned and/or sanitized to remove any previously collected dirt and microbial contamination.

When adhered to surface 12, multi-layer film 10 reduces the risk of additional microorganisms contacting and contaminating segment 12a of surface 12. First, multi-layer film 10 functions as a physical barrier that prevents microorganisms from contacting surface 12 at segment 12a. In addition, antimicrobial hardcoat layer 14, which includes one or more antimicrobial agents, biologically attacks microorganisms that come into contact with multi-layer film 10. This combination of physically blocking and biologically attacking microorganisms effectively reduces the risk of microbial contamination on segment 12a of surface 12.

The antimicrobial agents of antimicrobial hardcoat layer 14 are dispersed within a cross-linked matrix, which substantially prevents or retards the antimicrobial agents from being washed out of multi-layer film 10. Additionally, the cross-linked matrix of antimicrobial hardcoat layer 14 is abrasion resistant, which imparts physical durability to segment 12a of surface 12 while multi-layer film 10 is applied. Abrasion resistance is particularly beneficial for use with surfaces that are continuously subjected to wear and scratching. Antimicrobial hardcoat layer 14 retains its integrity while being subjected to such conditions to prevent damage to core layer 16 and/or adhesive layer 18, and to prevent the antimicrobial agents from being undesirably extracted from the cross-linked matrix.

In some embodiments, multi-layer film 10 is a thin, transparent film, which allows multi-layer film 10 to be adhered to surfaces (e.g., surface 12) without detracting from the visual and topographical characteristics of the surfaces. For example, multi-layer film 10 may be laminated on ornamental tables without detracting from the aesthetic qualities of the given tables. Additionally, multi-layer film 10 is particularly suitable for display applications, such as touch-screen displays. Multi-layer film 10 may be adhered over an entire screen surface of a touch-screen display, thereby allowing antimicrobial hardcoat layer 14 to provide protection against microbial contamination when users operate the touch-screen display.

Alternatively, multi-layer film 10 may be a colored, transparent film or an opaque film. Multi-layer film 10 may be printed or otherwise decorated with patterns and/or alphanumeric characters to impart information. The decorative pattern may be applied beneath antimicrobial hardcoat layer 14 and on top of core layer 16, or other intervening layers such that antimicrobial hardcoat layer 14 protects the information.

As further shown in FIG. 1, multi-layer film 10 has an overall layer thickness 10t, which includes thickness 14t of antimicrobial hardcoat layer 14, thickness 16t of core layer 16, and thickness 18t of adhesive layer 18. Examples of suitable thicknesses for overall layer thickness 10t range from about 50 micrometers to about 1,000 micrometers, with particularly suitable thickness ranging from about 80 micrometers to about 250 micrometers. Examples of suitable thicknesses for thickness 14t of antimicrobial hardcoat layer 14 range from about 1 micrometer to about 25 micrometers. Similarly, examples of suitable thicknesses for thickness 16t of core layer 16 range from about 40 micrometers to about 250 micrometers. Suitable thicknesses for thickness 18t of adhesive layer 18 may vary depending on the type of adhesive materials used and adhesive properties desired. Examples of suitable thicknesses for thickness 18t of adhesive layer 18 range from about 10 micrometer to about 50 micrometers.

As discussed above, antimicrobial hardcoat layer 14 includes antimicrobial agents that are dispersed or dissolved within the cross-linked matrix. The cross-linked matrix may be derived from any type of polymerizable precursor that is compatible with the incorporated antimicrobial agent(s). Examples of suitable polymerizable precursors for use in antimicrobial hardcoat layer 14 include radiation-curable materials, such as polymerizable monomers, polymerizable polymers having molecular weights of about 1,000 or less (e.g., oligomers and macromonomers), ceramer compositions thereof, and combinations thereof. Particularly suitable polymerizable polymers of the polymerizable precursor have molecular weights of about 500 or less, and even more particularly suitable polymerizable polymers of the polymerizable precursor have molecular weights of about 200 or less. The term "radiation curable" refers to functionality directly or indirectly pendant from the backbone that reacts (i.e., cross-links) upon exposure to a suitable source of curing energy. Suitable radiation cross-linkable groups for the polymerizable precursors include epoxy groups, (meth)acrylate groups (acryl and methacryl groups), olefinic carbon-carbon double bonds, allyloxy groups, alpha-methyl styrene groups, (meth)acrylamide groups, cyanate ester groups, vinyl ethers groups, and combinations thereof.

The polymerizable precursors may be monofunctional or multifunctional (e.g., di-, tri-, and tetra-) in terms of radiation-curable moieties. Examples of suitable monofunctional polymerizable precursors include styrene, alpha-methylstyrene, substituted styrene, vinyl esters, vinyl ethers, N-vinyl-2-pyrrolidone, (meth)acrylamide, N-substituted (meth)acrylamide, octyl(meth)acrylate, nonylphenol ethoxylate (meth)acrylate, isononyl(meth)acrylate, isobornyl(meth)acrylate, 2-(2-ethoxyethoxy)ethyl(meth)acrylate, 2-ethylhexyl(meth)acrylate, lauryl(meth)acrylate, beta-carboxyethyl(meth)acrylate, isobutyl(meth)acrylate, cycloaliphatic epoxide, alpha-epoxide, 2-hydroxyethyl(meth)acrylate, (meth)acrylonitrile, maleic anhydride, itaconic acid, isodecyl(meth)acrylate, dodecyl(meth)acrylate, n-butyl(meth)acrylate, methyl (meth)acrylate, hexyl(meth)acrylate, (meth)acrylic acid, N-vinylcaprolactam, stearyl (meth)acrylate, hydroxy functional caprolactone ester(meth)acrylate, isooctyl(meth)acrylate, hydroxyethyl(meth)acrylate, hydroxymethyl(meth)acrylate, hydroxypropyl(meth)acrylate, hydroxyisopropyl (meth)acrylate, hydroxybutyl(meth)acrylate, hydroxyisobutyl(meth)acrylate, tetrahydrofurfuryl(meth)acrylate, pentaerythritol pentaacrylate, pentaerythritol hexaacrylate and combinations thereof.

Examples of suitable multifunctional polymerizable precursors include ethylene glycol di(meth)acrylate, hexanediol di(meth)acrylate, triethylene glycol di(meth)acrylate, tetraethylene glycol di(meth)acrylate, trimethylolpropane tri(meth)acrylate, ethoxylated trimethylolpropane tri(meth)acrylate, glycerol tri(meth)acrylate, pentaerythritol tri(meth)acrylate, pentaerythritol tetra(meth)acrylate, and neopentyl glycol di(meth)acrylate, and combinations thereof.

Examples of suitable radiation-curable oligomers for the polymerizable precursor include oligomers based on urethane and polyester chemistries. Examples of commercially available (meth)acrylated urethanes and polyesters include oligomers commercially available under the trade designation "PHOTOMER" from Henkel Corp., Hoboken, N.J.; oligomers commercially available under the trade designation "EBECRYL" from UCB Radcure Inc., Smyrna, Ga.; oligomers commercially available under the trade designation "SARTOMER CN" from Sartomer Co., Exton, Pa.; oligomers commercially available under the trade designation "ACTILANE" from Akcross Chemicals, New Brunswick, N.J.; and oligomers commercially available under the trade designation "UVITHANE" from Morton International, Chicago, Ill.

Examples of suitable ceramer compositions for the polymerizable precursor include those disclosed in Craig et al., U.S. Pat. No. 6,299,799 ("the '799 patent"), particularly the ceramer composition described in Example 3 of the '799 patent. Examples of commercially available ceramer compositions include the trade designated "3M 906" Abrasion Resistant Hardcoat, and the trade designated "SCOTCH-GARD" UV-curable film protector coating, both of which are available from 3M Corporation, St. Paul, Minn.

Additional examples of commercially available polymerizable precursors include the trade designated "UVHC3000" materials from GE Silicones, Waterford, N.Y. In addition to the polymerizable precursors, the cross-linked matrix may also include one or more non-curable materials, such as non-curable polyurethanes, acrylic material, polyesters, polyimides, polyamides, epoxies, polystyrene (e.g., substituted polystyrene-containing materials), silicone containing materials, fluorinated materials, and combinations thereof.

In some embodiments, the polymerizable precursor also includes one or more curing agents, such as chain extension agents and radiation cross-linking agents (e.g., photoinitiators). The type of curing agent used depends on the polymerizable precursor used and on the wavelength of the radiation used to cure the polymerizable precursor. Examples of suitable commercially available free-radical generating photoinitiators include benzophenone, benzoin ether, and acylphosphine photoinitiators, such as those sold under the trade designations "IRGACURE" and "DAROCUR" from Ciba Specialty Chemicals, Tarrytown, N.Y. Co-initiators and amine synergists may also be included to improve curing rates. Suitable concentrations of the curing agent in the cross-linking matrix range from about 1% by weight to about 10% by weight, with particularly suitable concentrations ranging from about 2% by weight to about 5% by weight, based on the entire weight of the polymerizable precursor.

The polymerizable precursor may also include inorganic oxide fillers to increase mechanical and durability properties of the cross-linked matrix, such as hardness, modulus, abrasion resistance, and refractive index, as compared to unfilled systems. The presence of inorganic oxide particles may also decrease both shrinkage upon curing and the coefficient of thermal expansion of the resulting cured composition. Examples of suitable inorganic oxide fillers include acrylate-treated silica particles, such as those disclosed in Wu et al., U.S. Pat. No. 6,467,897. Examples of suitable concentrations of inorganic oxide fillers in the cross-linked matrix range from about 0.1% by weight to about 50% by weight, with particularly suitable concentrations ranging from about 5% by weight to about 25% by weight.

Inorganic oxide fillers may absorb part of the incident radiation during a curing process, thereby depleting the available energy to activate the curing agents. This may slow down the curing rate and may result in poor through and/or surface cure of the cross-linked matrix. To account for this, a mixture of curing agents may be used to provide both surface and through cure.

The polymerizable precursor may also include optional additives, such as heat stabilizers, ultraviolet light stabilizers, fragrances, free-radical scavengers, dyes, pigments, surfactants, and combinations thereof. Examples of suitable commercially available ultraviolet light stabilizers include benzophenone-type ultraviolet absorbers, which are available under the trade designation "UVINOL 400" from BASF Corp., Parsippany, N.J.; under the trade designation "CYASORB UV-1164" from Cytec Industries, West Patterson, N.J.; and under the trade designations "TINUVIN 900", "TINUVIN 123" and "TINUVIN 1130" from Ciba Specialty Chemicals, Tarrytown, N.Y. Examples of suitable concentrations of ultraviolet light stabilizers in the polymerizable precursor range from about 0.1% by weight to about 10% by weight, with particularly suitable total concentrations ranging from about 1% by weight to about 5% by weight.

Examples of suitable free-radical scavengers include hindered amine light stabilizer (HALS) compounds, hydroxylamines, sterically hindered phenols, and combinations thereof. Examples of suitable commercially available HALS compounds include the trade designated "TINUVIN 292" from Ciba Specialty Chemicals, Tarrytown, N.Y., and the trade designated "CYASORB UV-24" from Cytec Industries, West Patterson, N.J. Examples of suitable concentrations of free-radical scavengers in the polymerizable precursor range from about 0.05% by weight to about 0.25% by weight.

Examples of suitable surfactants include anionic, cationic, non-ionic, and zwitterionic surfactants and emulsifiers, such as those disclosed in Scholz et al., U.S. Pat. No. 5,951,993. Examples of suitable surfactants include polyalkoxylated block copolymer surfactants, silicone copolyols, polyethylene oxide alkyl and/or aryl ethers and esters, and combinations thereof.

Suitable antimicrobial agents for use in antimicrobial hardcoat layer 14 include any inorganic or organic antimicrobial agent that is effective for reducing or retarding contamination by microorganisms. Examples of suitable inorganic antimicrobial agents include transition metal ion-based compounds, (e.g., silver, zinc, copper, gold, tin and platinum-based compounds). Examples of suitable silver-containing antimicrobial agents include silver sulfate, silver acetate, silver chloride, silver lactate, silver phosphate, silver stearate, silver thiocyanate, silver proteinate, silver carbonate, silver nitrate, silver sulfadiazine, silver alginate, silver nanoparticles, silver-substituted ceramic zeolites, silver complexed with calcium phosphates, silver-copper complexed with calcium phosphates, silver dihydrogen citrates, silver iodines, silver oxides, silver zirconium phosphates, silver-substituted glass, and combinations thereof.

Suitable commercially available silver-containing antimicrobial agents include silver zeolites, such as those sold under the trade designation "AGION" from AgION Technologies Inc., Wakefield, Mass.; those available under the trade designations "IRGAGUARD B5000" and "IRGAGUARD B8000", which are based on AgZn zeolites supplied by Ciba Specialty Chemicals, Tarrytown, N.Y.; as well as those available under the trade designation "ALPHASAN", which are silver sodium hydrogen zirconium phosphates, supplied by Milliken Chemicals, Spartanburg, S.C.

Examples of suitable organic antimicrobial agents include those that are non-reactive with the polymerizable precursor and those that react and chemically bind with the polymerizable precursor. Suitable non-reactive organic antimicrobial agents include polymeric quaternary ammonium salts such as 2-butenyldimethyl ammonium chloride polymers commercially available under the trade designation "POLYQUAT" from Arch Chemicals, Inc., Norwalk, Conn.; and available under the trade designation "BARDAC", from Lonza Group Ltd., Valais, Switzerland; phenolic compounds such as phenol and its derivatives, parabens, and triclosan, which has the chemical formula 2,4,4'-trichloro-2'-hydroxy diphenyl ether, and is commercially available from Ciba Specialty Chemicals, Tarrytown, N.Y.; parachlorometaxylenols, poly(iminoimidocarbonylimidocarbonyliminohexamethylene hydrochlorides), commercially available under the trade designation "VANTOCIL P" from Arch Chemicals, Inc., Norwalk, Conn.; biguanide compounds (e.g., halogenated hexidines such as chlorhexidine, chlorhexidine gluconate, and chlorhexidine acetate), polyhexamethylene biguanides, antimicrobial lipids such as those disclosed in Scholz et al., U.S. Publication No. 2005/0089539, which is incorporated herein by reference, antimicrobial acids (e.g., fatty acids, benzoic acids, and salicylic acids), antimicrobial natural oils (e.g., tea tree oils, and grape fruit seed extracts), and combinations thereof. Additional suitable non-reactive organic antimicrobial agents include organic salts of transition metals (i.e., organometallic antimicrobial agents), such as silver salts (e.g., silver lactate), copper salts (e.g., copper napthenate), zinc salts, and tin salts (e.g., trialkyl tin hydroxides and triaryl tin hydroxides).

Suitable antimicrobial lipids include, for example, fatty acid monoesters/monoethers. In some embodiments, the fatty acid monoesters/monoethers suitable for the antimicrobial agent are considered food grade and recognized as safe (GRAS) by the U.S. Food and Drug Administration (FDA). Such fatty acid monoesters/monoethers may be derived from C8 to C12 fatty acids such as glycerol monoesters of caprylic acid, capric acid, and lauric acid; propylene glycol monoesters of caprylic acid, capric acid, and lauric acid; and combinations thereof. Examples of suitable fatty acid monoesters include, but are not limited to, glycerol monolaurate commercially available under the trade designation "LAURICIDIN" from Med-Chem Laboratories, East Lansing, Mich.; glycerol monocaprylate commercially available under the trade designation "POEM M-100" from Riken Vitamin Ltd., Tokyo, Japan; glycerol monocaprate commercially available under the trade designation "POEM M-200" from Riken Vitamin Ltd.; propylene glycol monolaurate, propylene glycol monocaprylate, and propylene glycol monocaprate, all commercially available from Uniquema International, Chicago, Ill.; and combinations thereof.

Examples of suitable concentrations of the fatty acid monoesters/monoethers range from about 1.0% to about 30.0% by weight. Examples of particularly suitable concentrations of the fatty acid monoesters/monoethers in the composition range from about 5.0% to about 20.0% by weight.

The antimicrobial agent may also include an enhancer and/or a surfactant for use with the fatty acid monoesters/monethers, as discussed in Andrew et al., PCT application No. WO 00/71183, entitled "Antimicrobial Articles," and in Andrews et al., PCT Application No. WO01/43549, entitled "Fruit, Vegetable, and Seed Disinfectants," both of which are incorporated herein by reference in their entireties.

Suitable reactive organic antimicrobial agents include quaternary amine-functionalized ethylenically unsaturated monomers. Quaternary amine-functionalized ethylenically unsaturated monomers are beneficial for use in antimicrobial hardcoat layer 14 because they may polymerize with the polymerizable precursor. This allows the antimicrobial agent to be chemically bonded by polymerization to the cross-linked matrix, while still providing antimicrobial activity to reduce microorganism contamination. Examples of suitable quaternary amine-functionalized ethylenically unsaturated monomers include dimethylhexadecylammoniumethylacrylate halides (DMAEA-$C_{16}$ halides; e.g., dimethylhexadecylammoniumethylacrylate bromides (DMAEA-$C_{16}$Br)), dimethylhexadecylammoniumethylmethacrylate halides (DMAEMA-$C_{16}$ halides; e.g., dimethylhexadecylammoniumethylmethacrylate bromides (DMAEMA-$C_{16}$Br)), and derivatives thereof. Examples of suitable derivatives of DMAEA-$C_{16}$ halides and DMAEMA-$C_{16}$ halides include derivatives of DMAEA-$CO_6$Br and DMAEMA-$C_{16}$Br, as described below, but it should be understood that similar derivatives of other DMAEA-$C_{16}$ halides and DMAEMA-$C_{16}$ halides are within the spirit and scope of the present disclosure, and one of ordinary skill in the art would understand how to extend the description below to such other halides.

Suitable derivatives of DMAEMA-$C_{16}$Br have the following formula structure:

where suitable values for "n" range from 8-20, with particularly suitable values for "n" ranging from about 14-16. Such polymer-chain lengths allow the DMAEMA derivative to move enough within the cross-linked matrix while also preventing the DMAEMA derivative from phase separating from the resulting cross-linked matrix.

DMAEMA-$C_{16}$Br and its derivatives may be formed by combining dimethylaminoethylmethacrylate salt, acetone, 1-bromohexadecane, and optionally, an antioxidant. The mixture may be stirred for about 16 hours at about 35° C. and then allowed to cool to room temperature. The resulting white solid precipitate may then be isolated by filtration, washed with cold ethyl acetate, and dried under vacuum at 40° C.

Similarly, DMAEA-$C_{16}$Br and its derivatives may be formed by combining dimethylaminoethylacrylate, of acetone, 1-bromohexadecane, and optionally, an antioxidant. The mixture may be stirred for 24 hours at 35° C., and then allowed to cool to room temperature. The acetone may then be removed by rotary evaporation under vacuum at 40° C. The resulting solids may then be washed with cold ethyl acetate and dried under vacuum at 40° C.

The antimicrobial performance of antimicrobial hardcoat layer 14 may also be increased by incorporating two or more synergistic antimicrobial agents into the cross-linked matrix. An example of a suitable synergistic composition includes combining a quaternary amine-functionalized ethylenically unsaturated monomer, which bonds chemically into the cross-linked matrix, and an inorganic silver compound, which disperses within the cross-linked matrix. Typically, the quaternary amine-functionalized ethylenically unsaturated monomer provides faster antimicrobial activity against gram (+) bacteria, while silver compounds show slower but broader antimicrobial activity against both gram (+) and gram (−) bacteria, viruses, and fungi.

Suitable concentrations of the antimicrobial agent in antimicrobial hardcoat layer 14 include concentrations that are high enough to effectively reduce microbial contamination, and low enough such that the antimicrobial agent does not phase separate from the cross-linked matrix. Examples of suitable antimicrobial agent concentrations in antimicrobial hardcoat layer 14 generally range from about 1% by weight to about 30% by weight. However, the suitable concentrations may vary depending on the antimicrobial agent used, the polymerizable precursor used, and the desired level of antimicrobial activity.

Suitable concentration ranges for inorganic antimicrobial agents in antimicrobial hardcoat layer 14 range from about 1% by weight to about 20% by weight, with particularly suitable concentrations ranging from about 5% by weight to about 10% by weight. Such concentrations provide suitable antimicrobial activity without negatively impacting the properties of antimicrobial hardcoat layer 14. Similarly, suitable concentration ranges for the above-discussed DMAEA derivatives and DMAEMA derivatives in antimicrobial hardcoat layer 14 range from about 2.5% by weight to about 50% by weight, with particularly suitable concentrations ranging from about 5% to about 20%. For antimicrobial agents that polymerize with the polymerizable precursor (e.g., DMAEA derivatives and DMAEMA derivatives), the concentrations of the antimicrobial agents are based on the weight of the antimicrobial monomer units in the antimicrobial hardcoat layer 14.

While shown as a single layer, antimicrobial hardcoat layer 14 may alternatively be derived from multiple polymerized layers. In this embodiment, antimicrobial hardcoat layer 14 may include concentration gradients of antimicrobial agents, where the inner-most layers (closer to core layer 16) include higher concentrations of antimicrobial agents relative to the outer-most layers.

Core layer 16 is a support substrate that provides mechanical support to antimicrobial hardcoat layer 14 and adhesive layer 18 during manufacture and use. Depending on particular applications, core layer 16 may be rigid, semi-rigid, or flexible/conformable. Suitable materials for core layer 16 include any rigid, semi-rigid, and conformable polymeric materials, such as thermoplastic materials (e.g., polyolefins and polyethylene terephthalates). Particularly suitable materials include thermoplastic materials that are optically transparent as thin layers. Additionally, core layer 16 may be primed or otherwise treated to promote adhesion to antimicrobial hardcoat layer 14 and/or adhesive layer 18 (e.g., acrylic priming and corona treatments). When flexible/conformable materials are used for core layer 16, multi-layer film 10 may be adhered to a variety surface dimensions (e.g., planar and curved surfaces). Additionally, the conformability allows multi-layer film 10 to be wound up and provided as a roll, thereby providing consumers with a convenient means for using multi-layer film 10.

While shown as a single layer, core layer 16 may alternatively be derived from multiple layers of the same or different substrate materials. As such, core layer 16 may provide a variety of optical enhancement properties, such as antiglare, antifog, light polarization, limited or expanded optical wavelength transmission, reflectivity, and combinations thereof.

As discussed above, adhesive layer 18 allows multi-layer film 10 to be adhered to surfaces (e.g., surface 12). In some embodiments, as described below, adhesive layer 18 provides good adhesion to surface 12, while also being removable under moderate force without leaving a residue on surface 12 (e.g., removable and/or repositionable pressure sensitive adhesives). Examples of suitable materials for adhesive layer 18 include one or more adhesives based on acrylates, urethanes, silicones, epoxies, rubber based adhesives (including natural rubber, polyisoprene, polyisobutylene, and butyl rubber, block copolymers, and thermoplastic rubbers), and combinations thereof.

Examples of suitable acrylates include polymers of alkyl acrylate monomers such as methyl methacrylate, ethyl methacrylate, n-butyl methacrylate, methyl acrylate, ethyl acrylate, n-butyl acrylate, iso-octyl acrylate, iso-nonyl acrylate, 2-ethylhexyl acrylate, decyl acrylate, dodecyl acrylate, n-butyl acrylate, hexyl acrylate, and combinations thereof. Examples of commercially available block copolymers include those available under the trade designation "KRATON G-1657" from Kraton Polymers, Westhollow, Tex.

As described above, in some embodiments, adhesive layer 18 can include a removable and/or repositionable pressure sensitive adhesive. As used herein and in the appended claims, an adhesive is considered to be "removable," if after final application to an intended substrate, the sheet material can be removed without damage to the substrate at the end of the intended life of the article at a rate in excess of 7.62 meters/hour (25 feet/hour) by hand with the optional use of heat. In some embodiments, the removable pressure sensitive adhesive has a 180 degree peel strength (from a painted steel substrate employing a peel rate of 30.5 cm/min) of less than 8 N/cm, and more particularly less than 6 N/cm.

As used herein and in the appended claims, "repositionable" refers to the ability to be, at least initially, repeatedly adhered to and removed from a surface or substrate without substantial loss of adhesion capability. In some embodiments, the repositionable pressure sensitive adhesive has a peel strength, at least initially, to the substrate surface lower than that for a conventional aggressively tacky PSA.

Examples of suitable removable and repositionable pressure sensitive adhesives include those described in Hobbs et al., U.S. Publication No. 2005/0249791 and Cooprider et al., U.S. Pat. No. 5,571,617, both of which are incorporated herein by reference; and adhesives based on solid inherently tacky, elastomeric microspheres, such as those disclosed in Silver, U.S. Pat. No. 3,691,140, Merrill et al., U.S. Pat. No. 3,857,731, and Baker et al., U.S. Pat. No. 4,166,152; all of which are incorporated herein by reference.

In some embodiments, adhesive layer 18 includes an electrostatic charge. In some embodiments, the adhesive layer 18 itself is an electrostatic charge that can be imparted to the multi-layer film 10 (e.g., the core layer 16). Alternatively, in some embodiments, the adhesive layer 18 combines an electrostatic charge with other adhesive components. Multi-layer films 10 including an electrostatic adhesive layer 18 can have a permanent electrostatic charge and can exhibit electrostatic attraction to a wide variety of surfaces thereby allowing the film to be removably adhered to the desired surface, Permanent electrostatic charge can be imparted to the multi-layer film 10 (e.g., to the core layer 16, or to the adhesive layer 18) using corona charging (e.g., nitrogen or air), as described in Everaerts et al., U.S. Publication No. 2005/0000642, which is incorporated herein by reference.

In some embodiments, adhesive layer 18 includes one or more antimicrobials to provide an additional source of biocidal activity. This can extend the useful life of the multi-layer film 10, as described in Hobbs et al., U.S. Publication No. 2005/0249791. Examples of suitable antimicrobial agents and concentrations include those discussed above for antimicrobial hardcoat layer 14.

In some embodiments, the adhesive material of adhesive layer 18 exhibits sufficient optical quality and light stability such that the adhesive material does not yellow with time or upon weather exposure so as to degrade the viewing quality of the underlying surface (e.g., surface 12). The adhesive material may be applied using a variety of known coating techniques such as transfer coating, knife coating, spin coating, die coating and the like. Additional examples of suitable adhesive materials for use in adhesive layer 18 include those described in Draheim et al., U.S. Publication No. 2003/0012936. Several of such adhesive materials are commercially available under the trade designations "8141", "8142", and "8161" adhesives from 3M Corporation, St. Paul, Minn.

In addition, adhesive layer 18 may be substantially flat or comprise a topographical pattern. Topographical patterns are beneficial for bleeding air out from beneath multi-layer film 10 as it is applied to surface 12, thereby reducing the amount of trapped air pockets beneath multi-layer film 10. Examples of suitable topographical patterns are discussed in Sher et al., U.S. Pat. No. 6,911,243.

Multi-layer film 10 may also contain one or more tie layers to enhance adhesion of antimicrobial hardcoat layer 14 and/or adhesive layer 18 to core layer 16. Examples of suitable tie layer materials include extrudable polymers such as ethylene vinyl acetate polymers, modified ethylene vinyl acetate polymers (modified with acid, acrylate, maleic anhydride, individually or in combinations), and combinations thereof. The tie layer may also include blends of the above-discussed suitable tie layer materials with thermoplastic polymers. Tie layers for extrusion coating may also include materials such as polyethyleneimines, which are commonly used to enhance the adhesion of extrusion coated layers. Tie layers can be applied to core layer 16 by coextrusion, extrusion coating, laminating, or solvent coating processes. Examples of suitable layer thicknesses for the tie layers range from about 25 micrometers to about 100 micrometers.

Multi-layer film 10 may be formed by initially blending the antimicrobial agent and the polymerizable precursor. This may be performed with the use of a solvent, where the resulting blend may be agitated until well mixed to form a hardcoat mixture. The resulting hardcoat mixture may then be coated onto top surface 16a of core layer 16. The coating step may be performed in a variety of manners, such as rod coating, knife coating, curtain coating, gravature coating, roll coating, extrusion processes, and wet casting processes. If a solvent is present in the hardcoat mixture, the coated film may then be dried to remove the solvents.

Examples of suitable solvents for forming the hardcoat mixture include water, alcohols (e.g., ethanol and isopropanol), ketones (e.g., methyl ethyl ketone, cyclohexanone, and acetone), aromatic hydrocarbons, isophorone, butyrolactone, N-methylpyrrolidone, tetrahydrofuran, esters (e.g., lactates and acetates such as propylene glycol monomethyl ether acetate, diethylene glycol ethyl ether acetate, ethylene glycol butyl ether acetate, dipropylene glycol monomethyl acetate), iso-alkyl esters (e.g., isohexyl acetate, isoheptyl acetate, isooctyl acetate, isononyl acetate, isodecyl acetate, isododecyl acetate, isotridecyl acetate), and combinations thereof.

After drying, the polymerizable precursor may be polymerized to form antimicrobial hardcoat layer 14 secured to core layer 16. The energy source used for achieving polymerization of the radiation curable functionality may be actinic (e.g., radiation having a wavelength in the ultraviolet or visible region of the spectrum), accelerated particles (e.g., electron beam radiation), or thermal (e.g., heat or infrared radiation). Suitable sources of actinic radiation include mercury lamps, xenon lamps, carbon arc lamps, tungsten filament lamps, lasers, electron beam energy, sunlight, and the like. A suitable commercially available ultraviolet-radiation system is a Fusion Systems UV Processor, Model MC6RQN, which is commercially available from Fusion UV Systems, Gaithersburg, Md.

The film may undergo one or more passes through the UV Processor to ensure substantial polymerization of antimicrobial hardcoat layer 14. The total radiation dose applied generally depends on the type of radiation source used, the thickness of antimicrobial hardcoat layer 14, and the chemistry of antimicrobial hardcoat layer 14. As discussed above, antimicrobial agents such as quaternary amine-functionalized ethylenically unsaturated monomers may also react with the polymerizable precursor.

After antimicrobial hardcoat layer 14 is polymerized, adhesive layer 18 may be laminated on bottom surface 16b of core layer 16 using standard lamination techniques. Multi-layer film 10 may also include a release liner (not shown) that is disposed on the exposed surface of adhesive layer 18, opposite of core layer 16. This protects adhesive layer 18 prior to use. Suitable release liners for use with multi-layer film 10 may be made of materials such as kraft papers, polyethylene, polypropylene, polyethylene, and combinations thereof. In some embodiments, the release liners are coated with compositions containing release agents, such as polymerized fluorochemicals or silicones. The low surface energy of the liner provides for an easy removal from adhesive layer 18.

Alternatively, an adhesive coated core layer may be coated with the antimicrobial hardcoat top layer 14 and cured.

Multi-layer film 10 may also include an end-of-service indicator to provide visual indication prompting the user to replace multi-layer film 10. Examples of suitable end-of-service indicators include time-temperature indicators and color changing dyes. An end-of-service indicator may be applied to multi-layer film 10 in the form of a label or paint to the corners of multi-layer film 10 after multi-layer film 10 is applied on surface 12. In some embodiments, the indicator is calibrated to indicate a color change at about the time when the corresponding multi-layer film 10 should be replaced (e.g., when the antimicrobial activity levels have substantially decreased).

Time-temperature indicators typically operate by chemical reaction mechanisms, diffusion mechanisms, and capillary driven, fluid-wicking mechanisms. Examples of suitable time-temperature indicators are disclosed in Bommarito, et al., U.S. Pat. No. 6,741,523 (i.e., microstructured time-dependent indicators) and Arens, et al., U.S. Pat. No. 5,667,303, both which are incorporated by reference in their entireties, and in *The Wiley Encyclopedia of Packaging Technology*, 400-406 (John Wiley & Sons, 1986) under the section entitled "Indicating Devices". Examples of suitable commercially available time-temperature indicators include those sold under the trade designations "MONITOR MARK" from 3M Corporation, St. Paul, Minn.; "WARM MARK" from Dry Pak Industries, Studio City, Calif.; "FRESH CHECK" from Lifelines Technology Inc., Morris Plains, N.J.; "VISTAB" from Visual Indicator Tag Systems AB, Malmö, Sweden; and "TT MONITOR" from Avery Dennison Corporation, Pasadena, Calif.

Multi-layer film 10 may be provided to an end user in a variety of arrangements. For example, multi-layer film 10 may be provided as a roll of tear-away film that allows consumers to remove desired amounts of multi-layer film 10 for individualized uses. Alternatively, multi-layer film 10 may be provided with pre-cut dimensions to fit industry standard components, such as touch-screen displays. Multi-layer film 10 may also be tailored to specific uses by varying the types and concentrations of the antimicrobial agents in antimicrobial hardcoat layer 14. For example, multi-layer film 10 may include antimicrobial agents that are effective against particular pathogens (e.g., gram positive or gram negative pathogens).

In use on a surface, multi-layer film 10 provides both physical and antimicrobial protection to the given surface. The abrasion resistance of antimicrobial hardcoat layer 14 protects the surface from physical damage while multi-layer film 10 is adhered to the surface. Additionally, the antimicrobial agents can reduce pathogenic contamination of the surface. Examples of suitable levels of antimicrobial activity include microbial load reductions of at least about 90% for at least one of *S. aureus* (gram positive) and *Ps. aeruginosa* (gram negative) pathogens. Examples of even more suitable levels of antimicrobial activity include microbial load reductions of at least about 99% for at least one of *S. aureus* (gram positive) and *Ps. aeruginosa* (gram negative) pathogens. Examples of particularly suitable levels of antimicrobial activity include microbial load reductions of at least about 90% for both of *S. aureus* (gram positive) and *Ps. aeruginosa* (gram negative) pathogens. Finally, examples of even more particularly suitable levels of antimicrobial activity include microbial load reductions of at least about 99% for both of *S. aureus* (gram positive) and *Ps. aeruginosa* (gram negative) pathogens. The "microbial load reductions" herein refer to microbial load reductions obtained pursuant to ASTM E2180-01.

When replacing multi-layer film 10, a user may peel multi-layer film 10 with a moderate force to delaminate adhesive layer 18 from the surface 12. The user may then dispose of the used multi-layer film 10, and adhere a second multi-layer film 10 to the surface 12 to further extend the period of protection against pathogen contamination. Alternatively, the multi-layer film 10 may be one of a plurality of multi-layer films 10 provided in a stack. The stack can then be adhered to the surface 12, and the uppermost multi-layer film 10 in the stack can be peeled from the stack to expose a fresh multi-layer film.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

The following compositional abbreviations are used in the following Examples:

"AgION": A silver-containing inorganic zeolite food-grade antimicrobial agent, type AJ, which contains 2.5% silver, and which is commercially available under the trade designation "AgION" Antimicrobial from AgION Technologies, Inc., Wakefield, Mass.

"Alphasan": A silver zirconium phosphate, commercially available under the trade designation "ALPHASAN RC 5000" from Milliken Chemicals, Spartanburg, S.C.

"Silver glass": A silver glass antimicrobial agent, commercially available from Giltech, Scotland, UK.

"Copper glass": A copper glass antimicrobial agent, commercially available from Giltech, Scotland, UK.

"Silver nanoparticles": A 20% silver nanoparticle dispersion in isopropanol, commercially available under the trade designation "SILVERJET DGP-(I)-20" from Advanced Nano Particles (ANP), Seoul, South Korea.

"Silver oxide": Silver oxide (AgO) having a formula weight of 123.9, commercially available from Alfa Aesar, Ward Hill, Mass.

"Ammonium Carbonate": Ammonium carbonate salt, commercially available from Aldrich, Milwaukee, Wis.

"Triclosan": Triclosan antimicrobial agent, commercially available from Ciba Specialty Chemicals., Tarrytown, N.Y.

"DMAEMA-CCl": Dimethylhexadecylammoniumethylmethacrylate-CCl antimicrobial agent, commercially available from Ciba Specialty Chemicals, Tarrytown, N.Y.

"Cosmocil CQ": An antimicrobial agent commercially available under the trade designation "COSMOCIL CQ" from Avecia, Inc., Wilmington Del.

"Vantocil P": A poly(iminoimidocarbonylimidocarbonyliminohexamethylene hydrochloride), commercially available under the trade designation "VANTOCIL P" from Arch Chemicals, Inc., Norwalk, Conn.

"Myacide AS Plus": An antimicrobial agent commercially available under the trade designation "MYACIDE AS PLUS" from BASF Corp., Parsippany, N.J.

"CHG": 20% chlorhexidine gluconate by weight in water, commercially available from Xttrium Laboratories, Inc., Chicago, Ill.

"Bardac 205M": A quaternary ammonium compound commercially available under the trade designation "BARDAC 205M" from Lonza Group Ltd., Valais, Switzerland.

"Bardac 208M": A quaternary ammonium compound commercially available under the trade designation "BARDAC 208M" from Lonza Group Ltd., Valais, Switzerland.

"3M 906 Hardcoat": A polymerizable precursor commercially available under the trade designation "3M 906" Abrasion Resistant Hardcoat, from 3M Corporation, St. Paul, Minn.

"3M SG composition": A polymerizable precursor commercially available under the trade designation "SCOTCHGARD" UV-curable film protector composition, from 3M Corporation, St. Paul, Minn.

"UVHC3000": A polymerizable precursor commercially available under the trade designation "UVHC3000", from GE Silicones, Waterford, N.Y.

"3M UV-Formulation": A polymerizable precursor containing 13.84 parts of an aliphatic urethane diacrylate diluted with 12% hexanediol diacrylate (commercially available under the trade designation "EBECRYL 284" from UCB Chemicals, Smyma, Ga.), 24.24 parts of iso-octyleacrylate (available from Sartomer Co., Exton, Pa.), 13.84 parts etrahydrofurfurylacrylate (also available from Sartomer Co.), 5 parts benzophenone free radical-generating photoinitiator (also available from Sartomer Co.), and 5 parts isopropylthioxanthone photoinitiator synergist (available from Aceto Corp., New Hyde Park, N.Y.).

"Irgacure 819": A phosphine oxide, phenyl bis(2,4,6-trimethyl benzoyl)) photoinitiator, commercially available under the trade designation "IRGACURE 819", from Ciba Specialty Chemicals, Tarrytown, N.Y.

"PET film": A polyethylene terephthalate film with acrylate-primed layer, commercially available from Mitsubishi, Japan.

"BOPP Film": A biaxially-oriented, corona-treated, polypropylene film available from 3M Corporation, St. Paul, Minn.

"Lauricidin": A glycerol monolaurate fatty acid monoester, commercially available under the trade designation "LAURICIDIN" from Med-Chem Laboratories, East Lansing, Mich.

"DOSS surfactant": A dioctylsulfosuccinate (DOSS) surfactant, commercially available from Alfa Aesar, Ward Hill, Mass.

"Salicylic acid": A 2-hydroxybenzoic acid ($HOC_6HgCO_2H$) with a formula weight of 138.1, commercially available from Sigma-Aldrich Chemical Company, Saint Louis, Mo.

Synthesis of Dimethylhexadecylammoniumethylmethacrylate Bromide Derivatives:

Dimethylhexadecylammoniumethylmethacrylate bromide (DMAEMA-$C_{16}$Br), which is a quaternary amine-functionalized ethylenically unsaturated monomer, was synthesized pursuant to the following procedure. A 500-milliliter round-bottom flask was charged with 42.2 parts of dimethylaminoethylmethacrylate salt, 154.7 parts of acetone, 93.2 parts of 1-bromohexadecane, and 0.34 parts of BHT antioxidant. The mixture was stirred for 16 hours at 35° C. and then allowed to cool to room temperature. The resulting white solid precipitate was isolated by filtration, washed with cold ethyl acetate, and dried under vacuum at 40° C. An NMR analysis of the solid product revealed the structure to be pure DMAEMA-$C_{16}$Br, having the following formula structure:

Similarly, $C_6$, $C_8$, $C_{12}$, and $C_{18}$ derivatives of DMAEMA were also synthesized pursuant to the above-described procedure.

Preparation of Silver Oxide Solution

Silver oxide solutions for use in Examples 6 and 28 below were prepared by combining S parts ammonium carbonate salt with 95 parts water, and mixing until the salt was dissolved. To this solution, 1 part silver oxide was added. The mixture was stirred at 60° C. for one hour until the silver oxide was dissolved.

Adhesive Layers

For the following Examples and Comparative Examples, adhesive layers were not laminated on the opposing sides of the core layer for any of the films. The following tests discussed below measured antimicrobial activity and abrasion resistance, both of which principally involve the antimicrobial hardcoat layers. It is believed that the use of adhesive layers made of conventional adhesives would not affect the antimicrobial activity or abrasion resistance, and that multi-layer films of the below-described Examples and Comparative Examples that include such adhesive layers would produce similar results.

Examples 1-11 and Comparative Examples A and B

Multi-layer films of Examples 1-11 and Comparative Examples A and B were each prepared pursuant to the following procedure. A hardcoat mixture was initially prepared by combining 100 parts of 3M 906 Hardcoat with 12 parts toluene and 12 parts methyl ethyl ketone. The hardcoat mixture was shaken gently until well blended. An antimicrobial agent was then added to the hardcoat mixture, and the entire mixture was shaken by hand. Table 1 lists the type and concentration of antimicrobial agent used in the hardcoat mixture for Examples 1-11 and Comparative Examples A and B.

TABLE 1

| Example | Antimicrobial Agent | Percent by Weight of Antimicrobial Agent |
|---|---|---|
| Example 1 | AgION | 5 |
| Example 2 | Silver glass | 5 |
| Example 3 | Copper glass | 5 |
| Example 4 | Copper glass | 10 |
| Example 5 | Silver nanoparticles | 10 |
| Example 6 | Silver oxide solution | 2 |
| Example 7 | DMAEMA-$C_{16}$Br | 10 |
| Example 8 | DMAEMA-$C_8$Br | 10 |
| Example 9 | DMAEMA-$C_8$Br | 30 |
| Example 10 | Triclosan | 5 |
| Example 11 | Silver glass | 10 |
| Comparative Example A | None | 0 |
| Comparative Example B | DMAEMA-CCl | 10 |

Each hardcoat mixture was then coated onto a PET film using a Meyer rod #8. The coated film was then allowed to air dry at room temperature for 5 minutes, followed by oven drying at 70° C. for 5 minutes (to remove the solvents). After drying, the hardcoat mixture was then cured (i.e., polymerized) using a Fusion Systems UV Processor operating at 100% power (model MC6RQN, commercially available from Fusion UV Systems, Gaithersburg, Md.). The processor was operated with an H-type bulb. The belt speed of the coated film was 50 feet per minute, and two passes were made, which provided a total radiation dose of 240 milliJoules/centimeter$^2$. This resulted in a two-layer film having an antimicrobial hardcoat layer laminated on a PET core layer, where the antimicrobial hardcoat layer contained an antimicrobial agent and a cross-linked matrix of 3M 906 Hardcoat. The films of Examples 1-11 and Comparative Examples A and B were each tested for microbial load reduction and for zones of inhibition.

The "microbial load reduction" was tested pursuant to ASTM E2180-01, which involved inoculation of a molten (45° C.) agar slurry with a standardized culture of bacterial cells. A thin layer of the inoculated agar slurry (0.5 milliliter) was then pipetted onto the test material and the untreated control material. Samples were tested in duplicate using *Staphylococcus aureus* (ATCC 6538) and *Pseudomonas aeruginosa* (ATCC 9027). After 24 hours, surviving microorganisms were recovered via elution of the agar slurry inoculum from the test substrate into D/E Neutralizing broth and extracted by sonication and vortexing. Serial dilutions were then made, and pour plates were made of each dilution. Agar plates were incubated for 48 hours at 28° C.±1° C. Bacterial colonies from each dilution series were then counted and recorded. Calculation of percent reduction of bacteria from treated versus untreated samples was then made. A percent reduction greater than 99.95% was reported as 100%.

The "zone of inhibition" test was performed by preparing separate solutions of *Staphylococcus aureus* (ATCC 6538) and *Pseudomonas aeruginosa* (ATCC 9027) at a concentration of approximately 1×10$^8$ colony forming units (cfu) per milliliter in Phosphate Buffered Saline (PBS) using a 0.5 McFarland Equivalence Turbidity Standard. These suspensions were used to prepare bacterial lawns by dipping a sterile cotton applicator into the solution and swabbing the surface of a trypticase soy agar (TSA) plate in three different directions. Separate plates were prepared for each organism. Three 7-millimeter disks from each sample were then placed onto the surface of an inoculated plate for each organism and pressed firmly against the agar with sterile forceps to ensure complete contact with the agar. The plates were then incubated at 28° C.±1° C. for 24 hours. The area under and surrounding the samples was then examined for bacterial growth. The zone of inhibition is reported as the diameter of the zone including the 7-mm sample disk. Table 2 provides the microbial load reduction results and the zone of inhibition results for the films of Examples 1-11 and Comparative Examples A and B.

TABLE 2

| | Microbial Load Reduction | | Zone of Inhibition S. aureus (Gram Positive) | |
|---|---|---|---|---|
| Example | % Reduction S. aureus (Gram Positive) | % Reduction Ps. aeruginosa (Gram Negative) | Zone Size | Growth under Sample |
| Example 1 | 99.7 | 100.0 | None | Heavy growth |
| Example 2 | 66.5 | 100.0 | None | Moderate growth |
| Example 3 | 93.5 | 100.0 | None | Moderate growth |
| Example 4 | 100.0 | 100.0 | None | Moderate growth |
| Example 5 | 79.1 | 100.0 | None | Moderate growth |
| Example 6 | 99.9 | 100.0 | None | Moderate growth |
| Example 7 | 100.0 | 7.4 | None | Moderate growth |
| Example 8 | 56.8 | 0.0 | None | Moderate growth |

TABLE 2-continued

|  | Microbial Load Reduction | | Zone of Inhibition S. aureus (Gram Positive) | |
|---|---|---|---|---|
| Example | % Reduction S. aureus (Gram Positive) | % Reduction Ps. aeruginosa (Gram Negative) | Zone Size | Growth under Sample |
| Example 9 | 99.2 | 35.4 | None | Light growth |
| Example 10 | 81.1 | 73.4 | 31 mm | No growth |
| Example 11 | 98.7 | 100.0 | 9 mm | No growth |
| Comparative Example A | 0.0 | 0.0 | None | Heavy growth |
| Comparative Example B | 0.0 | 0.0 | None | Moderate growth |

The microbial load reduction results in Table 2 show that the films of Examples 1-9 and 11 exhibited good antimicrobial activity against pathogens in contact with the films. It is noted that the films of Examples 7-9 exhibited low reductions against gram negative pathogens. The films of Examples 7-9 included DMAEMA derivative antimicrobial agents, which are generally poor antimicrobials against gram negative pathogens. Note that examples 8 and 9 have the same antimicrobial agent but at different concentrations. Increasing the DMAEMA derivative concentration from 10% to 30% resulted in improved kill against gram positive bacteria. With respect to the film of Comparative Example B, the DMAEMA-CCl antimicrobial agent is not reactive, and therefore did not polymerize with the 3M 906 Hardcoat. This resulted in phase separation and lack of antimicrobial activity.

The zone of inhibition results in Table 2 show low inhibition of bacterial growth for the films of Examples 1-9. This shows that the antimicrobial agents were retained by the cross-linked 3M 906 Hardcoat, and were not easily solubilized. Therefore, they did not diffuse out of the antimicrobial hardcoat layer to generate a zone of inhibition. This is desirable for long term antimicrobial activity. Additionally, the films of Examples 10 & 11 exhibited good antimicrobial activity against pathogens in direct contact with the films, thereby reducing pathogen contamination at locations under the given films.

Example 12

A multi-layer film of Example 12 was prepared pursuant to the following procedure. A dispersion was prepared by combining 95 parts by weight of 3M SG composition with 5 parts AgION to provide a hardcoat mixture. The hardcoat mixture was shaken by hand to form a uniform dispersion, and then coated on a PET film using a Meyer rod #6. The hardcoat mixture was then cured using a Fusion Systems UV Processor (discussed above) at a belt speed of 45 feet per minute with two passes, which provided a total radiation dose of 250 milliJoules/centimeter$^2$. This resulted in a two-layer film having an antimicrobial hardcoat layer laminated on a PET core layer, where the antimicrobial layer contained an AgION antimicrobial agent and a cross-linked matrix of 3M SG composition.

The film of Example 12 was tested for microbial load reduction and for zones of inhibition, as discussed above in Examples 1-11. The film of Example 12 exhibited a 100% microbial load reduction for both S. aureus (gram positive) and Ps. aeruginosa (gram negative). Additionally, the zone of inhibition testing did not show any growth under the sample. These results show desirable performance of this composition where the antimicrobial is retained by the polymerized 3M SG composition, while also providing a 100% microbial load reduction when contacted with contaminated fluids.

Example 13

A multi-layer film of Example 13, which included two antimicrobial agents, was prepared pursuant to the following procedure. A hardcoat mixture was prepared by combining 5 parts silver glass, 10 parts DMAEMA-C$_{16}$Br, and 85 parts 3M 906 Hardcoat. The hardcoat mixture was then coated on a PET film and cured pursuant to the procedure discussed above for Examples 1-11.

The film of Example 13 was also tested for microbial load reduction and for zones of inhibition, as discussed above in Examples 1-11. The film of Example 13 exhibited a 100% microbial load reduction for both S. aureus (gram positive) and Ps. aeruginosa (gram negative). Zone of inhibition testing showed no growth under the sample with S. aureus, moderate growth with Ps. aeruginosa, and no inhibition zones outside the sample disks. These results demonstrate the synergistic performance of the combined system where the silver has some mobility out of the film with excellent performance against gram positive bacteria, while the DMAEMA-C$_{16}$Br is chemically bonded by polymerization to the 3M 906 Hardcoat to provide good performance against gram positive bacteria for extended periods of time.

Examples 14-16 and Comparative Examples C and D

Multi-layer films of Examples 14-16 and Comparative Examples C and D were each prepared pursuant to the following procedure. A hardcoat mixture was prepared by combining DMAEMA-C$_{16}$Br, Irgacure 819, and 3M 906 Hardcoat in isopropanol to form a hardcoat mixture (40% solids by weight in the isopropanol). The hardcoat mixture was shaken to dissolve the solids and mix thoroughly. Table 3 provides the component concentrations of the hardcoat mixtures for the films of Examples 14-16 and Comparative Examples C and D.

TABLE 3

| Example | Percent by Weight of DMAEMA-C$_{16}$Br | Percent by Weight of 3M 906 Hardcoat | Percent by Weight of Irgacure 819 |
|---|---|---|---|
| Example 14 | 5.00 | 94.00 | 1.00 |
| Example 15 | 2.50 | 96.50 | 1.00 |
| Example 16 | 1.25 | 97.75 | 1.00 |
| Comparative Example C | 0.60 | 98.40 | 1.00 |
| Comparative Example D | 0.00 | 99.00 | 1.00 |

Approximately one milliliter of the hardcoat mixture was applied by pipette onto an acrylate-primed PET film. A wire-wound rod applicator (model AR4108 from BYK-Gardner) was used to spread the solution evenly down the length of the PET film. The hardcoat mixture was then allowed to dry by evaporation at room temperature, and then cured using a Fusion Systems UV Processor (discussed above). The Processor included a D-bulb using the following four types of UV light: UV-A (3.494 W/cm$^2$, 0.601 J/cm$^2$), UV-B (0.815 W/cm$^2$, 0.151 J/cm$^2$), UV-C (0.071 W/cm$^2$, 0.012 J/cm$^2$), and UV-D (1.733 W/cm$^2$, 0.307 J/cm$^2$). The film was passed through the Processor at a belt speed of 60 feet per minute with three passes, under nitrogen.

The films of Examples 14-16 and Comparative Examples C and D were tested in duplicate against a negative control for their antimicrobial effect on *Staphylococcus epidermidis*, a bacterium commonly found on human skin. For each film, a one inch sample was die cut and placed on glass slides inside a petri dish. A suspension of bacteria was prepared from an overnight culture (~$10^8$ colony forming units/milliliter (cfu/ml)), and 50 microliters was of the suspension was pipetted across the film sample surface in tiny droplets (generally 15-20 droplets). After incubating at room temperature, for 45 minutes, the film sample was then dropped into 20 milliliters of Neutralizing Buffer, vortexed vigorously for 2 minutes, diluted, and then plated in TSA (Trypticase Soy Agar) for enumeration of surviving bacteria.

The antimicrobial efficacy was calculated by subtracting the bacteria recovered from the test films (log 10 cfus) from the amount of bacteria recovered from the control (untreated) films. The limit of detection of this method, based on the volumes plated, was 20 cfu or 1.3 logs. Accordingly, higher log reductions correspond to higher antimicrobial efficacy. Table 4 provides the antimicrobial efficacy test results for the films of Examples 14-16 and Comparative Examples C and D.

TABLE 4

| Example | Percent by Weight of DMAEMA-$C_{16}$Br | Antimicrobial Data | Antimicrobial Effect |
|---|---|---|---|
| Example 14 | 5.00 | 6.42 log reduction | Total microbial kill |
| Example 15 | 2.50 | 1.96 log reduction | Partial microbial kill |
| Example 16 | 1.25 | 0.25 log reduction | Low microbial kill |
| Comparative Example C | 0.60 | 0.00 log reduction | No microbial kill |
| Comparative Example D | 0.00 | 0.00 log reduction | No microbial kill |

The results in Table 4 show concentration effects of DMAEMA-$C_{16}$Br on antimicrobial activity. In general, the antimicrobial activity is proportional to the concentration of DMAEMA-$C_{16}$Br in the 3M 906 Hardcoat. The results also show that a DMAEMA-$C_{16}$Br concentration below about 1% is ineffective for reducing pathogenic contamination, and a concentration of at least about 5% provides a total microbial kill (below the limit of detection).

Examples 17-21 and Comparative Examples E-J

Multi-layer films of Examples 17-21 and Comparative Examples E-J were each prepared pursuant to the following procedure. For the film of Comparative Example E, a hardcoat mixture was prepared by combining Irgacure 819 and 3M 906 Hardcoat in isopropanol. The resulting hardcoat mixtures for Comparative Example E had relative concentrations by weight of 1% Irgacure 81% and 99% 3M 906 Hardcoat. For each of the films of Examples 17-19 and Comparative Examples F and G, a hardcoat mixture was prepared by combining a DMAEMA-derivative antimicrobial agent, Irgacure 819, and 3M 906 Hardcoat in isopropanol. The hardcoat mixture was shaken to dissolve the solids and mix thoroughly. The resulting hardcoat mixtures had relative concentrations by weight of 5% DMAEMA-salt, 1% Irgacure 819, and 94% 3M 906 Hardcoat.

For the film of Comparative Example H, a hardcoat mixture was prepared by combining Irgacure 819 and UVHC3000 in methyl ethyl ketone. The resulting hardcoat mixtures for Comparative Example H had relative concentrations by weight of 1% Irgacure 819 and 99% UVHC3000. For the films of Examples 20 and 21, and Comparative Examples I and J, a hardcoat mixture was prepared by combining a DMAEMA-based antimicrobial agent, Irgacure 819, and UVHC3000 in methyl ethyl ketone. The hardcoat mixture was shaken to dissolve the solids and mix thoroughly. The resulting hardcoat mixtures had relative concentrations by weight of 5% DMAEMA-salt, 1% Irgacure 819, and 94% UVHC3000.

Table 5 provides the component listings of the hardcoat mixtures for the films of Examples 17-21 and Comparative Examples E-J.

TABLE 5

| Example | Antimicrobial Agent | Polymerizable Precursor |
|---|---|---|
| Comparative Example E | None | 3M 906 Hardcoat |
| Comparative Example F | DMAEMA-$C_6$Br | 3M 906 Hardcoat |
| Comparative Example G | DMAEMA-$C_8$Br | 3M 906 Hardcoat |
| Example 17 | DMAEMA-$C_{12}$Br | 3M 906 Hardcoat |
| Example 18 | DMAEMA-$C_{16}$Br | 3M 906 Hardcoat |
| Example 19 | DMAEMA-$C_{18}$Br | 3M 906 Hardcoat |
| Comparative Example H | None | UVHC3000 |
| Comparative Example I | DMAEMA-$C_6$Br | UVHC3000 |
| Comparative Example J | DMAEMA-$C_8$Br | UVHC3000 |
| Example 20 | DMAEMA-$C_{12}$Br | UVHC3000 |
| Example 21 | DMAEMA-$C_{16}$Br | UVHC3000 |

Approximately one milliliter of the hardcoat mixture was applied by pipette onto a PET film. A wire-wound rod applicator (model AR4108 from BYK-Gardner) was used to spread the solution evenly down the length of the PET film. The hardcoat mixture was then allowed to dry by evaporation at room temperature, and then cured using a Fusion Systems UV Processor (discussed above). The film was passed through the Processor at a belt speed of 30 feet per minute with one pass, under nitrogen.

For the films of Examples 17-19 and Comparative Examples E-G, the Processor included a D-bulb using the following four types of UV light: UV-A (5.000 W/cm$^2$, 2.328 J/cm$^2$), UV-B (1.577 W/cm$^2$, 0.782 J/cm$^2$), UV-C (0.144 W/cm$^2$, 0.105 j/cm$^2$), and UV-D (2.388 W/cm$^2$, 1.130 j/cm$^2$). For the films of Examples 20 and 21, and Comparative Examples H-J, the Processor included a D-bulb using the following four types of UV light: UV-A (5.000 W/cm$^2$, 2.308 J/cm$^2$), UV-B (1.531 W/cm$^2$, 0.737 j/cm$^2$), UV-C (0.151 W/cm$^2$, 0.094 J/cm$^2$), and UV-D (2.200 W/cm$^2$, 1.094 J/cm$^2$).

The films of Examples 17-21 and Comparative Examples E-J were tested in duplicate against a negative control for their antimicrobial effect on *Staphylococcus epidermidis*, a bacterium commonly found on human skin. For each film, a one inch sample was die cut and placed on glass slides inside a petri dish. A suspension of bacteria was prepared from an overnight culture (~$10^8$ cfu/milliliter), and 50 microliters was of the suspension was pipetted across the film sample surface in tiny droplets (generally 15-20 droplets). After incubating at room temperature for 45 minutes, the film sample was then dropped into 20 milliliters of Neutralizing Buffer, vortexed vigorously for 2 minutes, diluted, and then plated in TSA (Trypticase Soy Agar) for enumeration of surviving bacteria.

The antimicrobial efficacy was calculated by subtracting the bacteria recovered from the test films (log 10 cfus) from the amount of bacteria recovered from the control (untreated) films. The limit of detection of this method, based on the volumes plated, was 20 cfu or 1.3 logs. Accordingly, higher log reductions correspond to higher antimicrobial efficacy. Table 6 provides the antimicrobial efficacy test results for the films of Examples 17-21 and Comparative Examples E-J.

TABLE 6

| Example | Antimicrobial Agent | Antimicrobial Data | Antimicrobial Effect |
|---|---|---|---|
| Comparative Example E | None | 0.15 Log reduction | No microbial kill |
| Comparative Example F | DMAEMA-$C_6$Br | 0.03 Log reduction | No microbial kill |
| Comparative Example G | DMAEMA-$C_8$Br | 0.06 Log reduction | No microbial kill |
| Example 17 | DMAEMA-$C_{12}$Br | 0.84 Log reduction | Low microbial kill |
| Example 18 | DMAEMA-$C_{16}$Br | 6.49 Log reduction | Total microbial kill |
| Example 19 | DMAEMA-$C_{18}$Br | 0.38 Log reduction | Low microbial kill |
| Comparative Example H | None | 0.18 Log reduction | No microbial kill |
| Comparative Example I | DMAEMA-$C_6$Br | 0.16 Log reduction | No microbial kill |
| Comparative Example J | DMAEMA-$C_8$Br | 0.15 Log reduction | No microbial kill |
| Example 20 | DMAEMA-$C_{12}$Br | 1.49 Log reduction | Partial microbial kill |
| Example 21 | DMAEMA-$C_{16}$Br | 6.49 Log reduction | Total microbial kill |

The results in Table 6 show how the polymer chain length of the DMAEMA derivatives affects the antimicrobial activity. As shown, DMAEMA derivatives of DMAEMA-$C_8$Br and smaller at 5% concentrations in the polymerizable precursors effectively provided no antimicrobial activity. In contrast, the DMAEMA-$C_{16}$Br for both polymerizable precursors used provided the highest level of antimicrobial activity, which generally shows the optimal polymer chain length for DMAEMA derivatives. Accordingly, DMAEMA derivatives having polymer chain lengths similar to DMAEMA-$C_{16}$Br are long enough to be sufficiently mobile within the cross-linked matrix, and are also short enough to prevent phase separating from the cross-linked matrix.

The films of Examples 17, 18, 20, and 21 were also tested for abrasion resistance pursuant to ASTM F735-94. Each sample film was placed in a 16-ounce jar and covered with 50 grams of 20-30 mesh Ottawa sand (VWR Bristol, Conn.). The jar was then placed in an orbital shaker (VWR, DS-500E, from VWR Bristol, Conn.), which was set at 400 rpm for one hour. The haze and transmission of the sample were measured before and after testing using a Haze-Guard Plus (BYK-Gardner, HB-4725). Table 7 provides the durability testing results (i.e., haze and transmission) for the films of Examples 17, 18, 20, and 21.

TABLE 7

| | Before Test | | After Test | | Change | |
|---|---|---|---|---|---|---|
| Example | Haze | Transmission | Haze | Transmission | Haze | Transmission |
| Example 17 | 0.59 | 92.9 | 3.48 | 93.0 | 2.88 | 0.1 |
| Example 18 | 0.47 | 93.0 | 4.25 | 93.0 | 3.78 | 0.0 |
| Example 20 | 0.78 | 93.0 | 9.59 | 92.7 | 8.81 | -0.3 |
| Example 21 | 1.31 | 92.9 | 10.3 | 92.7 | 8.99 | -0.2 |

The results in Table 7 show that the inclusion of 5% the DMAEMA derivatives did not significantly impact the abrasion resistance of the films. As a result, the antimicrobial hardcoat layers of the multi-layer films of the present invention protect underlying surfaces from physical damage while also reducing pathogenic contamination.

Example 22

A multi-layer film of Example 22 was prepared pursuant to the following procedure. A hardcoat mixture was prepared by combining 5.0 grams of DMAEMA-$C_{16}$Br, and 197.9 grams of a 3M 906 Hardcoat solution (47.5% solids in isopropanol, where 1% of the solids was Irgacure 819), and 47.1 grams of isopropanol. The hardcoat mixture was shaken to dissolve the solids and mix thoroughly. The resulting hardcoat mixtures had a 5:95 ratio of DMAEMA-$C_{16}$Br to 3M 906 Hardcoat.

The hardcoat mixture was then coated onto a PET film (4-inch width) with a metered, precision die coating process to achieve a dry thickness of 4 micrometers. A syringe pump was used to set the flow rate of the hardcoat mixture into the coating die at 10.5 cubic-centimeters/minute. The coated film was then passed through a two-zone oven and a belt speed of 15 feet per minute. Each zone of the oven was maintained at 120° C. and was 3 meters in length. The coated hardcoat mixture was then cured using a Fusion Systems UV Processor (discussed above). The Processor included an H-bulb using the following four types of UV light: UV-A (1.696 W/cm$^2$, 1.049 J/cm$^2$), UV-B (1.561 W/cm$^2$, 0.994 J/cm$^2$), UV-C (0.206 W/cm$^2$, 0.137 J/cm$^2$), and UV-D (0.965 W/cm$^2$, 0.606 J/cm$^2$).

The film of Example 22 was tested for abrasion resistance pursuant to ASTM F735-94. Three samples of each film (referred to as A, B, and C) were each placed in a 16-ounce jar and covered with 50 grams of 20-30 mesh Ottawa sand (VWR Bristol, Conn.). The jar was then placed in an orbital shaker (VWR, DS-500E, from VWR Bristol, Conn.), which was set at 400 rpm for one hour. The haze and transmission of the sample were measured before and after testing using a Hazegard plus (BYK-Gardner, HB-4725). Table 8 provides the durability testing results (i.e., haze and transmission) for the film of Example 22.

TABLE 8

| | Before Test | | After Test | | Change | |
|---|---|---|---|---|---|---|
| Example | Haze | Transmission | Haze | Transmission | Haze | Transmission |
| Example 22A | 0.64 | 92.7 | 3.28 | 92.6 | 2.64 | -0.1 |
| Example 22B | 0.64 | 92.5 | 3.31 | 92.2 | 2.67 | -0.3 |
| Example 22C | 0.61 | 92.6 | 3.26 | 92.4 | 2.65 | -0.2 |

The results shown in Table 8 also show that the inclusion of DMAEMA-$C_{16}$Br did not significantly impact the abrasion resistance of the films. As discussed above for the films of Examples 17-21, the antimicrobial hardcoat layers of the multi-layer films of the present invention protect underlying surfaces from physical damage.

Examples 23-31

Multi-layer films of Examples 23-25 were each prepared pursuant to the following procedure. For each film, the antimicrobial agent was added to a 50/50 blend of toluene/methyl ethyl ketone solvent, and sonicated to obtain a uniform dispersion. 3M 906 hardcoat was then mixed in with the dispersion to form a hardcoat mixture. Table 12 provides the component listings of the hardcoat mixtures for the films of Examples 23-25.

TABLE 12

| Example | Antimicrobial Agent | Percent by Weight of Antimicrobial Agent | Percent by Weight of 3M 906 Hardcoat | Percent by Weight of Tolune/MEK Solvent Blend |
|---|---|---|---|---|
| Example 23 | DMAEMA-$C_{16}$Br | 5.9 | 70.6 | 23.6 |
| Example 24 | AgION | 3.6 | 72.3 | 24.0 |
| Example 25 | DMAEMA-$C_{16}$Br/ AgION | 3.0/1.8 | 71.4 | 23.8 |

For each film of Examples 23-25, the hardcoat mixture was coated on a PET film using a Meyer rod #8. The coated film was allowed to air dry at room temperature for 5 minutes, and then was oven dried at 70° C. for 5 minutes. The coating was cured using a Fusion Systems UV Processor (discussed above) with an H-bulb. The coated film was passed through the UV processor twice with a belt speed of 50 feet per minute, which provided a total radiation dose of 240 milli-Joules/centimeter$^2$.

Multi-layer films of Examples 26-31 were each prepared pursuant to the following procedure. For each film, the antimicrobial agent was directly mixed with the 3M 906 Hardcoat, and the resulting mixture was diluted with isopropanol to form a hardcoat mixture. Table 13 provides the component listings of the hardcoat mixtures for the films of Examples 26-31.

TABLE 13

| Example | Antimicrobial Agent | Percent by Weight of Antimicrobial Agent | Percent by Weight of 3M 906 Hardcoat | Percent by Weight of Isopropanol |
|---|---|---|---|---|
| Example 26 | Cosmocil CQ | 15.0 | 54.0 | 31.0 |
| Example 27 | Vantocil P | 15.0 | 54.0 | 31.0 |
| Example 28 | Myacide AS Plus | 3.0 | 54.0 | 43.0 |
| Example 29 | CHG | 3.0 | 58.8 | 38.2 |
| Example 30 | Bardac 205M | 9.0 | 51.0 | 40.0 |
| Example 31 | Bardac 208M | 5.6 | 51.0 | 43.4 |

For each film of Examples 26-31, the hardcoat mixture was coated on a PET film using a Meyer rod #9. The coated film was allowed to air dry at room temperature for 5 minutes, and then was oven dried at 80° C. for 5 minutes. The coating was cured using a Fusion Systems UV Processor (discussed above) with an H-bulb (1.98 J/cm$^2$) The coated film was passed through the UV processor twice.

The resulting multi-layer films of Example 23-31 were then tested for microbial load reduction, as discussed above in Examples 1-11. Table 14 provides the microbial load reduction results and visual appearance results for the films of Examples 23-31.

TABLE 14

| Example | % Reduction S. aureus (Gram Positive) | % Reduction Ps. aeruginosa (Gram Negative) | Film Appearance |
|---|---|---|---|
| Example 23 | 100.0 | 33.3 | Clear, uniform, and glossy |
| Example 24 | 96.2 | 100.0 | Clear, uniform, with slight haze |
| Example 25 | 100.0 | 100.0 | Clear, uniform, with slight haze |
| Example 26 | 100.0 | 100.0 | Clear, uniform, very little haze |

TABLE 14-continued

| Example | % Reduction S. aureus (Gram Positive) | % Reduction Ps. aeruginosa (Gram Negative) | Film Appearance |
|---|---|---|---|
| Example 27 | 100.0 | 100.0 | Clear, uniform, very little haze |
| Example 28 | 0.0 | 100.0 | Clear, uniform |
| Example 29 | 100.0 | 100.0 | Clear, uniform |
| Example 30 | 100.0 | 100.0 | Clear, uniform |
| Example 31 | 100.0 | 100.0 | Clear, uniform |

The results in Table 14 show that the films of Examples 23-31 exhibited good antimicrobial activity against pathogens in contact with the films. The film containing Myacide AS Plus (Example 28) exhibited no antimicrobial activity against gram positive pathogens. This indicates that Myacide AS Plus is only effective against gram negative pathogens at the tested concentration.

The films of Examples 23-31 were also generally clear, uniform, and transparent. This shows that the antimicrobial agents were compatible with the 3M 906 Hardcoat, and exhibited little or no phase separation.

Examples 32-35

Multi-layer films of Examples 32-35 were each prepared pursuant to the following procedure. For each film, the antimicrobial agent was blended with the 3M UV-Formulation. The blended composition was sonicated to obtain a uniform dispersion. Table 15 provides the component listings of the blended composition for the films of Examples 32-35.

TABLE 15

| Example | Antimicrobial Agent | Percent by Weight of Antimicrobial Agent | Percent by weight of 3M UV-Formulation |
|---|---|---|---|
| Example 32 | DMAEMA-C16Br | 4.8 | 95.2 |
| Example 33 | AgION | 2.9 | 97.1 |
| Example 34 | DMAEMA-C16Br | 9.1 | 90.9 |
| Example 35 | DMAEMA-C16Br/ AgION | 7.3/1.8 | 90.9 |

For each film, the dispersion was coated on a PET film using a Meyer rod #6. The coating was then cured using a Fusion Systems UV Processor (discussed above) with an H-bulb. The coated film was passed through the UV processor once with a belt speed of 80 feet per minute, which provided a total radiation dose of 120 milliJoules/centimeter$^2$. The resulting multi-layer films of Example 32-35 were then tested for microbial load reduction, as discussed above in Examples 1-11. Table 16 provides the microbial load reduction results and visual appearance results for the films of Examples 32-35.

TABLE 16

| Example | % Reduction S. aureus (Gram Positive) | % Reduction Ps. aeruginosa (Gram Negative) | Film Appearance |
|---|---|---|---|
| Example 32 | 69.20 | 10.60 | Clear, uniform, and glossy |
| Example 33 | 83.00 | 100.00 | Clear, uniform, with slight haze |
| Example 34 | 100.00 | 89.20 | Clear, uniform, and glossy |
| Example 35 | 100.00 | 100.00 | Clear, uniform, with slight haze |

The results shown in Table 16 illustrate the need for a minimum concentration of the antimicrobial agent in the hardcoat for effective microbial load reduction. Moreover, a comparison of Examples 33 and 34 to Example 35 show that a synergistic effect can be obtained in microbial load reduction by combining two different types of antimicrobial agents.

Example 36

Synthesis of dimethylhexadecylammoniumethylacrylate bromide (DMAEA-C$_{16}$Br) was prepared pursuant to the following procedure. A three-neck round bottom reaction flask was fitted with a mechanical stirrer, temperature probe, and a condenser. The reaction flask was charged with 234 parts of dimethylaminoethylacrylate, 617 parts of acetone, 500 parts of 1-bromohexadecane, and 0.5 parts of BHT antioxidant. The mixture was stirred for 24 hours at 35° C. The reaction mixture was then cooled to room temperature and a slightly yellow clear solution was obtained. The solution was transferred to a round bottom flask and the acetone was removed by rotary evaporation under vacuum at 40° C. The resulting solids was washed with cold ethyl acetate and dried under vacuum at 40° C. An NMR analysis of the solid product revealed the structure to be pure DMAEA-C$_{16}$Br. The DMAEA-C$_{16}$Br was believed to provide similar antimicrobial activity to DMAEA-C$_{16}$Br when used in a multi-layer film of the present invention. An advantage provided by DMAEA-C$_{16}$Br over its methacrylate based version (DMAEMA-C$_{16}$Br) is faster radiation curing. This is due to the lack of methyl group near the ethylenically unsaturated bond (i.e., the reactive site of the monomer).

Example 37

A fluid solution of 20.0% Lauricidin, 10.0% salicylic acid, and 10.0% DOSS surfactant in isopropanol was prepared by stirring the mixture until the Lauricidin was dissolved. 20% of the fluid solution was combined with 80% of the hardcoat mixture described in Examples 1-11 (i.e., 100 parts of 3M 906 Hardcoat with 12 parts toluene and 12 parts methyl ethyl ketone). The combined solution was coated and cured as described in Examples 1-11. The resulting multi-layer film was clear and transparent. The resulting multi-layer film was then tested for microbial load reduction, as described above in Examples 1-11, and gave 100% microbial load reduction for gram positive pathogens and 99.4% microbial load reduction for gram negative pathogens.

The embodiments described above and illustrated in the figure are presented by way of example only and are not intended as a limitation upon the concepts and principles of the present invention. As such, it will be appreciated by one having ordinary skill in the art that various changes in form and detail are possible without departing from the spirit and scope of the present invention. Various features and aspects of the invention are set forth in the following claims.

The invention claimed is:

1. A multi-layer film for reducing microbial contamination on a surface, the multi-layer film comprising:
    a thermoplastic core layer having a first surface and a second surface opposite the first surface;
    an adhesive layer disposed adjacent the first surface of the core layer; and
    an antimicrobial hardcoat layer disposed adjacent the second surface, the antimicrobial hardcoat layer comprising an antimicrobial agent chemically bound to a cross-linked matrix, and inorganic particles chemically bound to the cross-linked matrix,
    wherein the cross-linked matrix is derived from a polymerizable precursor comprising a material selected from the group consisting of a polymerizable monomer, a polymerizable polymer having a molecular weight of about 1,000 or less, and combinations thereof; from about 5 wt % to about 20 wt % of a reactive antimicrobial agent; and reactive inorganic particles,
    wherein the reactive antimicrobial agent includes at least one of a dimethylalkylammoniumethylacrylate halide and a dimethylalkylammoniumethylmethacrylate halide, wherein the alkyl group has from 14 to 16 carbons.

2. The multi-layer film of claim 1, wherein the antimicrobial agent chemically bound to the cross-linked matrix is a first antimicrobial agent, and further comprising a second antimicrobial agent dispersed within the cross-linked matrix.

3. The multi-layer film of claim 2, wherein the second antimicrobial agent comprises a quaternary amine-functionalized compound.

4. The multi-layer film of claim 2, wherein the second antimicrobial agent comprises a silver-containing compound.

5. The multi-layer film of claim 2, wherein the second antimicrobial agent comprises a fatty acid monoester or a fatty acid monoether.

6. The multi-layer film of claim 2, wherein the second antimicrobial agent constitutes about 1% by weight to about 20% by weight of the antimicrobial layer.

7. The multi-layer film of claim 2, wherein the second antimicrobial agent constitutes about 4% by weight to about 10% by weight of the antimicrobial layer.

8. The multi-layer film of claim 1, wherein the antimicrobial layer exhibits a microbial load reduction of at least about 99% for either gram positive or gram negative pathogens, when tested pursuant to ASTM E2180-01.

9. The multi-layer film of claim 2, wherein the antimicrobial layer exhibits a microbial load reduction of at least about 99% for both gram positive and gram negative pathogens, when tested pursuant to ASTM E2180-01.

10. The multi-layer film of claim 2, wherein the material of the polymerizable precursor comprises a multi-functional acrylate.

11. The multi-layer film of claim 10, wherein the multi-functional acrylate is cross-linkable upon exposure to ultraviolet radiation.

12. The multi-layer film of claim 10, wherein the reactive inorganic particles comprise acrylate-treated inorganic particles.

13. The multi-layer film of claim 1, wherein the adhesive layer includes at least one of a removable adhesive, a repositionable adhesive, and an electrostatic charge.

14. The multi-layer film of claim 1, wherein the adhesive layer includes an antimicrobial.

15. A stack comprising a plurality of the multi-layer film of claim 1, the plurality of multi-layer films arranged such that the adhesive layer of a first multi-layer film is positioned adjacent the antimicrobial layer of a second multi-layer film.

16. The multi-layer film of claim 1, wherein the material of the polymerizable precursor comprises a multi-functional acrylate.

17. The multi-layer film of claim 16, wherein the reactive inorganic particles comprise acrylate-treated inorganic particles.

18. A method of making a hardcoat multi-layer film for reducing microbial contamination on a surface, the method comprising:
laminating an adhesive layer adjacent a first surface of a thermoplastic core layer;
coating an antimicrobial layer adjacent a second surface of the core layer, the second surface being opposite of the first surface, wherein the antimicrobial layer comprises from about 5 wt % to about 20 wt % of a reactive antimicrobial agent, reactive inorganic particles, and a polymerizable precursor comprising a material selected from the group consisting of a polymerizable monomer, a polymerizable polymer having a molecular weight of about 1,000 or less, and combinations thereof, wherein the reactive antimicrobial agent includes at least one of a dimethylalkylammoniumethylacrylate halide and a dimethylalkylammoniumethylmethacrylate halide, wherein the alkyl group has from 14 to 16 carbons; and
polymerizing the polymerizable precursor, the reactive antimicrobial agent, and the reactive inorganic particles to form an antimicrobial hardcoat layer comprising a cross-linked matrix, wherein the antimicrobial agent is chemically bound to the cross-linked matrix, and the inorganic particles are chemically bound to the cross-linked matrix.

19. The multi-layer film of claim 1, wherein the polymerizable precursor includes multi-functional radiation curable moieties.

20. The multi-layer film of claim 1, wherein the reactive inorganic particles include acrylate-treated silica particles.

21. The multi-layer film of claim 1, wherein the reactive antimicrobial agent includes monomers having the formula:

wherein n ranges from 14 to 16.

22. The multi-layer film of claim 1, wherein the reactive antimicrobial agent includes at least one of a dimethylhexadecylammoniumethylacrylate halide and a dimethylhexadecylammoniumethylmethacrylate halide.

23. The multi-layer film of claim 1, wherein the polymerizable precursor includes a multifunctional polymerizable precursor that includes three or four radiation curable moieties.

24. The multi-layer film of claim 1, wherein the reactive antimicrobial agent includes at least one of a dimethylhexadecylammoniumethylacrylate bromide and a dimethylhexadecylammoniumethylmethacrylate bromide.

25. The method of claim 18, wherein the reactive antimicrobial agent includes monomers having the formula:

wherein n ranges from 14 to 16.

26. The method of claim 18, wherein the reactive antimicrobial agent includes at least one of a dimethylhexadecylammoniumethylacrylate halide and a dimethylhexadecylammoniumethylmethacrylate halide.

27. The method of claim 18, wherein the reactive antimicrobial agent includes at least one of a dimethylhexadecylammoniumethylacrylate bromide and a dimethylhexadecylammoniumethylmethacrylate bromide.

28. The method of claim 18, wherein the polymerizable precursor includes a multifunctional polymerizable precursor that includes three or four radiation curable moieties.

29. The method of claim 18, wherein the reactive inorganic particles include acrylate-treated silica particles.

* * * * *